United States Patent [19]
Koyama et al.

[11] Patent Number: 6,087,401
[45] Date of Patent: Jul. 11, 2000

[54] CYCLOPENTENONES, PROCESS FOR PREPARING THE SAME, AND THE USE THEREOF

[75] Inventors: Nobuto Koyama; Hiroaki Sagawa; Eiji Kobayashi; Tatsuji Enoki; Hua-Kang Wu; Eiji Nishiyama; Katsushige Ikai; Ikunoshin Kato, all of Otsu, Japan

[73] Assignee: Takara Shuzo Co., Ltd., Kyoto, Japan

[21] Appl. No.: 09/230,868

[22] PCT Filed: Sep. 1, 1997

[86] PCT No.: PCT/JP97/03052

§ 371 Date: Feb. 2, 1999

§ 102(e) Date: Feb. 2, 1999

[87] PCT Pub. No.: WO98/13328

PCT Pub. Date: Apr. 2, 1998

[30] Foreign Application Priority Data

| Sep. 27, 1996 | [JP] | Japan | 8-275231 |
| Nov. 22, 1996 | [JP] | Japan | 8-325900 |
| Feb. 25, 1997 | [JP] | Japan | 9-055434 |
| Mar. 28, 1997 | [JP] | Japan | 9-092866 |
| Apr. 21, 1997 | [JP] | Japan | 9-116045 |

[51] Int. Cl.[7] .................................................. A61K 31/12
[52] U.S. Cl. ........................... 514/690; 568/346; 568/379
[58] Field of Search .............................. 514/690; 568/346, 568/379

[56] References Cited

U.S. PATENT DOCUMENTS

| 5,116,869 | 5/1992 | Sugiura et al. | 514/456 |
| 5,149,711 | 9/1992 | Hazato et al. | 514/548 |

FOREIGN PATENT DOCUMENTS 1-233255  9/1989  Japan .
2-247151 10/1990  Japan .

OTHER PUBLICATIONS

Ahmad et al., "The formation of reductic acid from pentoses or hexuronic acids", Carbohydr. Res. (1993), 247, pp. 217–222.

Cocu et al., "Cyclitols. XLIV. Synthesis of cycloses derived from cyclopentane", Helv. Chim. Acta (1972), 55(8), pp. 2838–2844.

Langenfeld, et al., "D–Moenuronic acid (4–methyl–D–glucuronic acid), a new building block for the antibiotic meonomycin A", Tetrahedron Lett. (1978), (21), pp. 1833–1836.

*Primary Examiner*—James H. Reamer
*Attorney, Agent, or Firm*—Wenderoth, Lind & Ponack, L.L.P.

[57] ABSTRACT

There is disclosed a method of manufacturing 4,5-dihydroxy-2-cyclopenten-1-one represented by the following formula [1] which is characterized in that at least one substance selected from the following (a), (b) and (c) is heated.

(a): uronic acid or uronic acid derivative(s);

(b): a saccharide compound which contains uronic acid and/or uronic acid derivative(s); and (c): a substance containing a saccharide compound which contains uronic acid and/or uronic acid derivative(s).

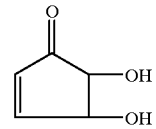

[1]

54 Claims, 15 Drawing Sheets

CYCLOPENTENONES, PROCESS FOR PREPARING THE SAME, AND THE USE THEREOF

TECHNICAL FIELD

The present invention relates to cyclopetenones having a physiological activity such as anticancer action and having a high safety and, more particularly, it relates to manufacturing methods of said compounds and also to pharmaceuticals containing said compounds as effective components. The present invention also relates to a series of inventions useful in the fields of food, beverage, etc.

PRIOR ART

Pharmaceuticals which have been used in clinical therapy include many agents such as anticancer agents, antibiotic substances, immunopotentiators, immunomodulators, etc. (such as alkylating agents, antimetabolites and plant alkaloids) but it is hardly said that such a drug therapy has been completely established already.

Among those agents, prostaglandin A and J having a cyclopentenone ring among the prostaglandins derived from natural substances have been reported to have a possibility of being used as highly-safe anticancer agents due to their inhibition of DNA synthesis and various derivatives of them have been synthesized (refer to the Japanese Laid-Open Patent Publication Sho-62/96438).

PROBLEMS TO BE SOLVED BY THE INVENTION

An object of the present invention is to develop highly-safe cyclopentenone compounds having physiological actions such as an anticancer action and to offer manufacturing methods for said compounds, pharmaceuticals having said compounds as effective components and food or beverage containing said compounds. Another object of the present invention is to offer a method of use of said compounds and also other compounds, etc. which are related to said compounds.

MEANS TO SOLVE THE PROBLEMS

The present invention will be summarized to be as follows. Thus, the first feature of the present invention relates to a method of manufacturing 4,5-dihydroxy-2-cyclopenten-1-one represented by the following formula [1] which is characterized in that at least one substance selected from the following (a), (b) and (c) is heated.

(a): uronic acid or uronic acid derivative(s);
(b): a saccharide compound which contains uronic acid and/or uronic acid derivative(s); and
(c): a substance containing a saccharide compound which contains uronic acid and/or uronic acid derivative(s).

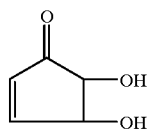

[1]

The second feature of the present invention relates to a method of manufacturing 4,5-dihydroxy-2-cyclopenten-1-one which is characterized in that at least one substance selected from the following (a), (b) and (c) is heated and the 4,5-dihydroxy-2-cyclopenten-1-one represented by the formula [1] is collected from the above heat-treated product.

(a): uronic acid or uronic acid derivative(s);
(b): a saccharide compound which contains uronic acid and/or uronic acid derivative(s); and
(c): a substance containing a saccharide compound which contains uronic acid and/or uronic acid derivative(s).

The third feature of the present invention relates to a method of manufacturing an optically active compound of 4,5-dihydroxy-2-cyclopenten-1-one which is characterized in including the following steps.

(A): a step wherein at least one substance selected from the following (a), (b) and (c) is heated to produce 4,5-dihydroxy- 2-cyclopenten-1-one.
  (a): uronic acid or uronic acid derivative(s),
  (b): a saccharide compound which contains uronic acid and/or uronic acid derivative(s), and
  (c): a substance containing a saccharide compound which contains uronic acid and/or uronic acid derivative(s);
(B): an optional step wherein 4,5-dihydroxy-2-cyclopenten-1-one is isolated from the resulting heat-treated product; and
(C): a step where 4,5-dihydroxy-2-cyclopenten-1-one is subjected to an optical resolution.

The fourth feature of the present invention relates to (−)-4,5-dihydroxy-2-cyclopenten-1-one having an optical rotation $[\alpha]_D^{20}$ −105° (c=0.30, ethanol).

The fifth feature of the present invention relates to (+)-4,5-dihydroxy-2-cyclopenten-1-one having an optical rotation $[\alpha]_D^{20}$ +104° (c=0.53, ethanol).

The sixth feature of the present invention relates to an anticancer agent which is characterized in containing 4,5-dihydroxy-2-cyclopenten-1-one represented by the formula [1] and/or an optically active compound thereof.

The seventh feature of the present invention relates to a cancer cell differentiation inducer which is characterized in containing 4,5-dihydroxy-2-cyclopenten-1-one represented by the formula [1] and/or an optically active compound thereof.

The eighth feature of the present invention relates to an apoptosis inducer which is characterized in containing 4,5-dihydroxy-2-cyclopenten-1-one represented by the formula [1] and/or an optically active compound thereof.

The ninth feature of the present invention relates to an antibacterial agent which is characterized in containing 4,5-dihydroxy-2-cyclopenten-1-one represented by the formula [1] and/or an optically active compound thereof.

The tenth feature of the present invention relates to a method for the induction of cancer cell differentiation which is characterized in using 4,5-dihydroxy-2-cyclopenten-1-one represented by the formula [1] and/or an optically active compound thereof as effective ingredient(s).

The eleventh feature of the present invention relates to a method for the induction of apoptosis which is characterized in using 4,5-dihydroxy-2-cyclopenten-1-one represented by the formula [1] and/or an optically active compound thereof as effective ingredient(s).

The twelfth feature of the present invention relates to food or beverage which is characterized in that 4,5-dihydroxy-2-cyclopenten-1-one represented by the formula [1] and/or an optically active compound thereof are/is contained therein, diluted thereby and/or added thereto.

The thirteenth feature of the present invention relates to a substance which contains a saccharide compound containing uronic acid and/or uronic acid derivative(s) which is characterized in that, in said substance which contains a saccharide compound containing uronic acid and/or uronic acid derivative(s), at least a part of reactivity of amines, amino acids, peptides or protein having a reactivity with uronic acid, uronic acid derivative(s), (an) intermediate(s) for 4,5-dihydroxy-2-cyclopenten-1-one represented by the formula [1] or 4,5-dihydroxy-2-cyclopenten-1-one represented by the formula [1] disappears and/or at least a part of said reactive substance(s) is removed.

The present inventors have found that the compound represented by the formula [1], i.e. 4,5-dihydroxy-2-cyclopenten-1-one (hereinafter, this will be just referred to as "the cyclopentenone"), is produced in a heat-treated products of at least one substance selected from uronic acid, uronic acid derivative(s), a saccharide compound containing uronic acid and/or uronic acid derivative(s) and a substance which contains a saccharide compound containing uronic acid and/or uronic acid derivative(s) and that said compound which is isolated from the heat-treated products has various physiological activity such as anticancer action, apoptosis-inducing action and antibacterial action and also have succeeded in preparing optically active substances of said compound whereupon the present invention has been achieved.

PREFERRED EMBODIMENTS OF THE INVENTION

Figure 1:
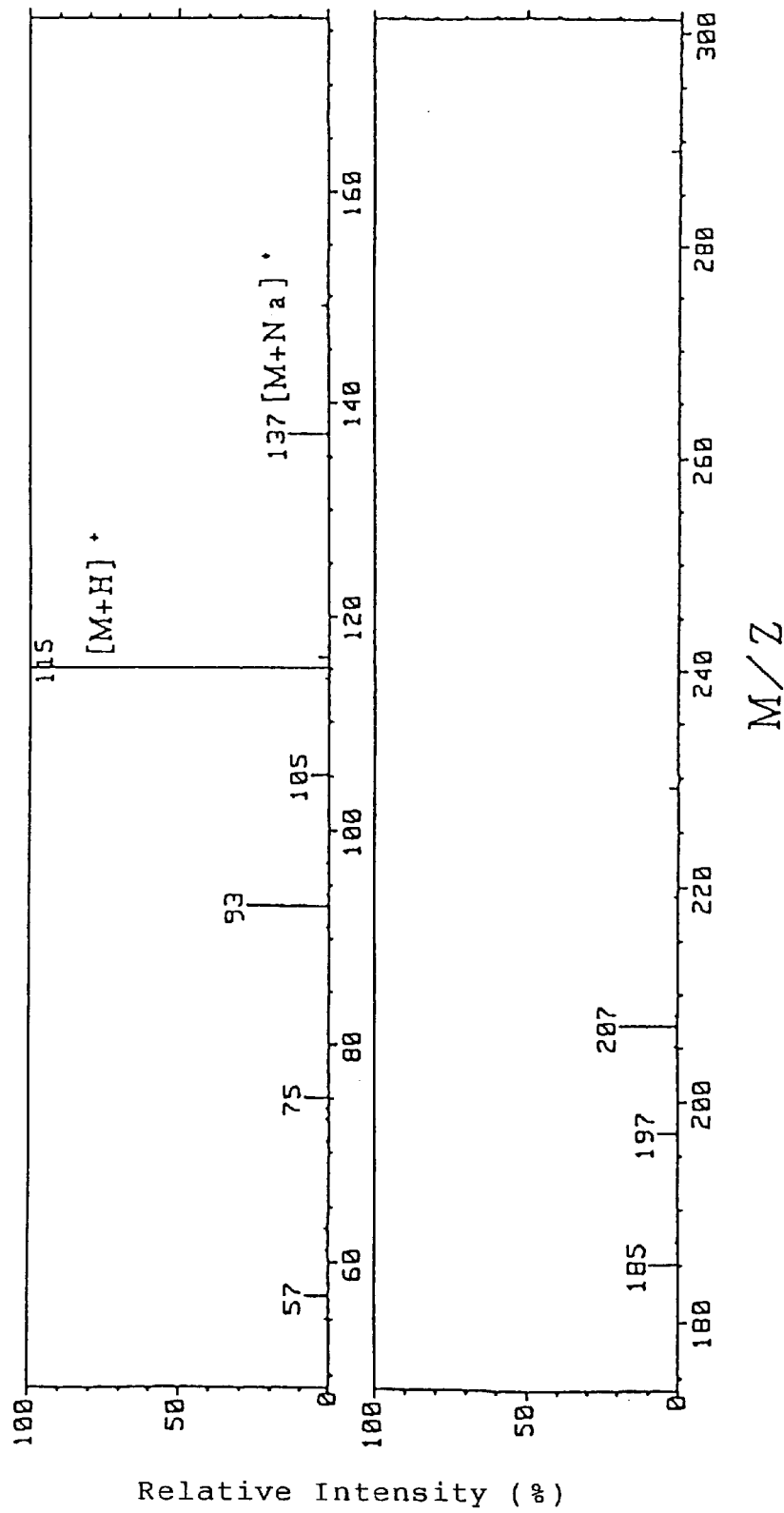
FIG. 1 shows a mass spectrum of the cyclopentenone.

The present invention will now be more specifically illustrated as hereinafter.

In the present invention, there is no particular limitation for uronic acid, uronic acid derivative(s), a saccharide compound containing uronic acid and/or uronic acid derivative(s) and a substance which contains a saccharide compound containing uronic acid and/or uronic acid derivative(s) so far as the cyclopentenone is produced in the heat-treated products thereof.

It is now possible in accordance with the present invention that an appropriate amount of the physiologically active cyclopentenone and/or optically active compound thereof are/is contained in food or beverage. As a result of anticancer action, antibacterial action, etc. of those compounds, the food or beverage of the present invention is quite useful as anticancer and antibacterial food or as anticancer and antibacterial beverage.

In addition, the present invention offers a pharmaceutical composition containing the cyclopentenone and/or optically active substance thereof and said pharmaceutical composition is useful as a therapeutic or a preventive agent for cancer and also as an antibacterial agent for antiseptics, antibacterial dentifrices, antibacterial cosmetics, antibacterial bathing agent, etc.

The present invention further offers a method for induction of cancer cell differentiation and also for induction of apoptosis by the use of the cyclopentenone and/or optically active substance thereof as effective ingredients and those methods are useful in biochemical research and in screening of pharmaceuticals such as cancer cell differentiating agents and apoptosis induction inhibitors.

The cyclopentenone used in the present invention can be produced by heating a substance selected from (a) uronic acid or uronic acid derivative(s); (b) a saccharide compound which contains uronic acid and/or uronic acid derivative(s) and (c) a substance containing a saccharide compound which contains uronic acid and/or uronic acid derivative (s). Accordingly, it is also possible to prepare the cyclopentenone of the present invention by heating (a), (b) or (c) which is produced from a material containing neither (a), (b) nor (c) by physical, chemical, enzymatic or other means.

It is also possible in the present invention to use the heated-treated products containing the cyclopentenone or the purified cyclopentenone or partially-purified cyclopentenone obtained from the above heat-treated products.

Uronic acid is sometimes called glycuronic acid and is a general name for hydroxyaldehyde carboxylic acids in which an aldehyde group on aldose remains as it is while only a primary alcohol group at another end is oxidized to a carboxyl group. It is present in nature as a constituting ingredient for various polysaccharides of animals and plants. Examples of the polysaccharide containing uronic acid are pectin, pectic acid, alginic acid, hyaluronic acid, heparin, heparan sulfate, fucoidan, chondroitin sulfate, chondroitin, dermatan sulfate, etc. and they have been known to exhibit various physiological functions.

There is no particular limitation for the uronic acid used in the present invention. Thus, examples of the uronic acid are galacturonic acid, glucuronic acid, guluronic acid, mannuronic acid and iduronic acid while examples of the uronic acid derivative(s) are lactones, esters, amides, salts, etc. of the above-mentioned ones and any substance which produces the cyclopentenone on heating is covered by the derivative of the present invention. Examples of the uronic acid lactone are glucurono- 6,3-lactone (hereinafter, abbreviated as glucuronolactone), mannurono-6,3-lactone and idurono-6,3-lactone. Examples of the uronic acid ester are methyl, ethyl, propylene glycol and carboxymethyl uronates which can be manufactured from uronic acid. Uronic acid amide can be manufactured by amidation of uronic acid. Salts of them can be manufactured by common methods.

There is no particular limitation for the saccharide compound containing uronic acid and/or uronic acid derivative(s) in this specification and the examples applicable are pectin, pectic acid, alginic acid, hyaluronic acid, heparin, heparan sulfate, fucoidan, chondroitin sulfate, chondroitin and dermatan sulfate including decomposed products, derivatives of the decomposed products and salts of the decomposed products thereof which are chemically, enzymatically or physically-treated products thereof.

In the above-mentioned chemical treatment, the starting compound is, for example, treated at room temperature to 200° C. for several seconds to several hours or, preferably, at 50–130° C. for several seconds to 60 minutes. When said treatment is conducted under acidic condition, glycoside bond is hydrolyzed and, in the case of pectin, a decomposed product containing galacturonic acid and/or galacturonic acid ester is resulted. Or, for example, when treated at pH 6.8, 95° C. for several minutes to several tens minutes, a beta-elimination takes place to give a saccharide compound having unsaturated uronic acid and/or unsaturated uronic acid ester in which an absorbance at around 235 nm is increased. The saccharide compound of the present invention covers a saccharide compound containing unsaturated uronic acid and/or unsaturated uronic acid ester at a non-reducing end prepared by a beta-elimination of a polysaccharide compound containing uronic acid and/or uronic acid ester.

An example of the above-mentioned enzymatic treatment is a known decomposition method in which the starting saccharide compound containing uronic acid and/or uronic acid ester is decomposed by a hydrolase such as pectinase and hyaluronidase for the saccharide containing uronic acid and/or uronic acid ester. Another example is a known decomposition method in which the saccharide containing uronic acid and/or uronic acid ester is decomposed by a lyase for the saccharide containing uronic acid and/or uronic acid ester. For example, in the case of pectin or pectic acid, a decomposition is conducted by a known pectin lyase (EC 4.2.2.10), pectiate lyase (EC 4.2.2.2) or exopolygalacturonic acid lyase (EC 4.2.2.9) to give a saccharide compound having 4-deoxy-L-threo-hex-4-enopyranosyl uronate or methyl ester thereof at a non-reducing end. In the case of hyaluronic acid, a hyaluronate lyase (EC 4.2.2.1) is used while, in the case of alginic acid, an alginate lyase (EC 4.2.2.3) is used. Incidentally, in the case of alginic acid, a saccharide compound having 4-deoxy-L-erythro-hex-4-enopyranosyl uronate at its non-reducing end is obtained. The enzymatically decomposed products having 4-deoxy-L-threo-hex-4-enopyranosyl uronate, 4-dexoy-L-erythro-hex-4-enophranosyl uronate or methyl ester thereof at the non-reducing end prepared as such are covered by the saccharide compound of the present invention as well.

Examples of the above-mentioned physical treatment are the treatment of the starting saccharide compound with near infrared ray, infrared ray, microwave, ultrasonic wave, etc. Thus, for example, pectin and/or pectic acid are/is placed in a neutral (in terms of pH) or an alkaline solution and subjected to an ultrasonic wave for applying a vibrational energy at an appropriate temperature of not lower than room temperature under an appropriate reductive operation, for example, in the presence of ascorbic acid for not shorter than one second or, preferably, from five seconds to one hour. Besides the ultrasonic wave, it is also effective to irradiate with microwave, near infrared ray, infrared ray, etc. or a combination thereof. The irradiation may be conducted either continuously or intermittently.

In the present invention, there is no particular limitation for the substance which contains a saccharide compound containing uronic acid and/or uronic acid derivative(s) so far as said substance contains a saccharide compound containing the above-mentioned uronic acid and/or uronic acid derivative(s). Examples of the substance which contains the saccharide compound containing uronic acid or uronic acid derivative(s) are as follows. Thus, fruits, vegetables, leaves, seeds, etc. of dicotyledonous plants such as apple, citrus fruits (e.g., mandarin orange and lemon), banana, nappa cabbage, cabbage, lettuce, perilla, pumpkin, celery, burdock, echalote, broccoli, green pepper, spinach, onion, carrot, leaves of carrot, leaves of daikon (Japanese radish), tea leaves, sesame, beans, potato, etc.; cereals of monocotyledonous plants such as wheat and rice; algae such as brown algae (e.g., sea tangle and wakame seaweed), red algae, green algae and unicellular green algae; microorganisms such as Basidiomycetes (e.g., Lyophyllum ulmarium, Lyophyllum decastes, Pholiota nameko, Cortinellus shiitake, Flammulina verutipes, Agaricus ostreatus and Pasalliota campestris), Ascomycetes (e.g., Cordyceps militaris and other Cordyceps sp.), yeasts, filamentous fungi (e.g., Aspergillus sp.) and bacteria (e.g., Bacillus natto and lactic acid bacteria); and animals such as vertebrate animals and invertebrate animals including skin of pigs, skin of cows, cartilage of shark, cartilage of whale, etc. In the present invention, a substance which contains a saccharide compound containing uronic acid and/or uronic acid derivatives derived from the above-mentioned plants, microorganisms or animals may be used.

Moreover, in the present invention, the following agricultural and fishery products or processed food products as they are or after drying/crushing may be used as the substance which contains a saccharide compound containing uronic acid and/or uronic acid derivative(s). They are rind of a fruit, strained lees of a fruit (such as those of apple and mandarin orange), strained lees of a vegetable, strained lees of cereals (such as those obtained in the preparation of sake [Japanese rice wine], beer, shochu [Japanese distilled spirits] and whiskey), strained lees of beans (such as okara [Japanese bean-curd refuse]) and strained lees of sea algae, etc.

The substance which contains a saccharide compound containing uronic acid and/or uronic acid derivative (s) used in the present invention may be used as it is or may be subjected to any of the conventional processes such as boiling, baking, parching, roasting, decocting, steaming, frying, deep-frying, etc. as a pretreatment.

Moreover, in the present invention, the substance which contains a saccharide compound containing uronic acid and/or uronic acid derivative(s) may be subjected to the above-mentioned chemical, enzymatic (including fermentational one using microorganisms) or physical pretreatment and the resulting substance treated as such or purified substance prepared from said resulting substance may be used as well.

The substance which contains a saccharide compound containing uronic acid and/or uronic acid derivative(s) contains a substance which is reactive with uronic acid, uronic acid derivative(s), intermediate(s) for the production of the cyclopentenone and substances reactive with the cyclopentenone such as amines, amino acids, peptides and/or protein and it is preferred for the manufacture of the cyclopentenone to conduct a pretreatment whereby at least a part of the reactivity of such reactive substances disappears and/or at least a part of said reactive substances is removed. There is no particular limitation for said pretreatment although a dry heating is preferred. For example, water is removed from the substance which contains a saccharide compound containing uronic acid and/or uronic acid derivative (s) and then heated at 60–400° C. for several seconds to several days to give the substance which contains a saccharide containing uronic acid and/or uronic acid derivative(s). It is suitable for the manufacture of the cyclopentenone or the optically active substance thereof of the present invention wherein the proteins, etc. are insolubilized, denatured or inactivated. An example of the method for the dry heating treatment is a roasting/parching treatment using hot air as mentioned in the Japanese Laid-Open Patent Publication Hei-02/79965 and, by said method, large amount of heat-treated substance, i.e. roasted/parched substance, can be efficiently prepared. There is no particular limitation for the roasted/parched substance and its examples are roasted/parched plants, animals and microorganisms such as roasted/parched vegetables, fruits, cereals, mushrooms, sea algae, cortex and cartilage. Another example is a fraction which is prepared by treating said saccharide-containing substance with protease followed by removing the decomposed protein therefrom. Other examples are a fraction obtained by crushing said saccharide-containing substance followed by washing with water, a fraction obtained by subjecting said saccharide-containing substance to a pretreatment with an acid and a fraction obtained by subjecting said saccharide-containing substance to a pretreatment with an alkali. All of the pretreated cyclopentenone-productive substances as such which are appropriate for the production of the cyclopentenone are covered by the substance which contains a saccharide compound containing uronic acid and/or uronic acid derivative(s) as defined by the present invention.

The intermediate for the production of the cyclopentenone mean(s) a substance which is produced during the heating treatment of uronic acid, uronic acid derivative(s), a saccharide compound containing uronic acid and/or uronic acid derivative(s) and the substance which contains a saccharide compound containing uronic acid and/or uronic acid derivative(s) and changes to the cyclopentenone upon further reaction. Examples of the intermediate for the production of the cyclopentenone are decarboxylated products of uronic acid, dehydrated products of uronic acid and decarboxylated/dehydrated products of uronic acid.

The polysaccharides which are saccharide compounds containing uronic acid and/or uronic acid derivative(s) can be manufactured by known chemical, enzymatic or physical methods. In the case of pectin for example, a high-molecular weight polysaccharide extracted from, for example, rind of citrus fruits or apple may be used. Materials for the manufacture of pectin on an industrial scale are fruits and, in addition to strained lees (mostly comprising endocarp) after preparing juice of citrus fruits such as lemon and lime, the strained lees after preparation of apple juice is used as well. Such strained lees mostly contain an insoluble protopectin and it is solubilized (extracted) during the course of manufacture to prepare pectin. Solubilization can be conducted by extracting with an acidic warm to hot water and, when the conditions such as temperature, pH and time in extracting are properly controlled depending upon the type of the starting material, it is possible to manufacture pectin having predetermined molecular weight and degree of esterification in a high yield. The extract is purified by means of centrifugation or filtration and concentrated and alcohol is added thereto whereupon pectin can be precipitated and recovered. The recovered precipitate is dried and crushed to prepare a dry pectin.

The main structure of pectin is a partially methylated galacturonic acid polymer. The carboxyl group is either methylesterified, left as a free acid or made into a salt such as ammonium salt, potassium salt or sodium salt. Depending upon the degree of methylesterification (DM; ratio of methoxyl groups to total carboxyl groups), pectin is classified into an HM pectin having a high DM and an LM pectin having a low DM ["Handbook of Materials for Developing New Food Products" edited by Satoshi Yoshizumi, et al., published by K. K. Korin, pages 114–119 (1991)] and, in the present invention, pectin which is commercially available as a food additive ["Handbook of Natural Products", edited by Akio Toyama, et al., published by Shokuhin To Kagakusha, 12th Edition, page 138 (1993)], commercially available HM pectin and LM pectin, etc. [refer to the above-mentioned "Handbook of Materials for Developing New Food Products"] may be used.

Uronic acid, uronic acid derivatives, oligosaccharides, etc. which are synthesized by a synthetic means may be used in the present invention as well.

The heat-treated substance used in the present invention may be manufactured using a substance selected from (a) uronic acid or uronic acid derivative(s), (b) a saccharide compound containing uronic acid and/or uronic acid derivative(s) and (c) a substance which contains a saccharide compound containing uronic acid and/or uronic acid derivative(s) as a starting material.

There is no particular limitation for the method of the heating treatment in the manufacture of the heat-treated substance used in the present invention so far as the cyclopentenone of the present invention can be produced. Thus, for example, uronic acid, uronic acid derivative(s), a saccharide compound containing uronic acid and/or uronic acid derivative(s) or a substance which contains a saccharide compound containing uronic acid and/or uronic acid derivative(s) is heated at 60–350° C. for several seconds to several days or, preferably, at 80–150° C. for several minutes to several days. In the case of pectin, a heat-treated substance containing the cyclopentenone can be obtained by heating, for example, at 80–150° C. for several minutes to several days. Alternatively, when uronic acid, uronic acid lactone or uronic acid ester is heated at 60–150° C. for several minutes to several days, a desired heat-treated substance containing the cyclopentenone can be obtained. Such a heat-treated substance contains trans-cyclopentenone and small amount of cis-cyclopentenone where the hydroxyl groups at the positions 4 and 5 are in trans and cis configurations, respectively. When the cyclopentenone purified from this heat-treated substance is made to react with acetic anhydride in anhydrous pyridine and the resulting 4,5-diacetylcyclopentenone is separated by a silica gel column chromatography followed by subjecting to a structural analysis of each of the fractions by means of nuclear magnetic resonance, it is confirmed that trans-cyclopentenone and small amount of cis-cyclopentenone are contained in this heat-treated substance.

There is no particular limitation for the pH upon the heating treatment and it is preferred to conduct under neutral to acidic conditions. The pH during the heating treatment may be adjusted depending upon the type of the materials used but, usually, production of the cyclopentenone is promoted by heating under an acidic condition.

There is no particular limitation for the concentrations of the materials upon the heating treatment so far as the concentrations are within such a range that the cyclopentenone can be produced and they may be set by taking operability, yield, etc. into consideration.

The heating treatment in the present invention may be either wet heating or dry heating although, in view of the productive efficiency of the cyclopentenone of the present invention, a wet heating is preferred. In the case of a wet heating, any of wet heating methods such as heating with steam, heating with steam under high pressure, heating under high pressure, etc. may be used while, in the case of a dry heating, any of dry heating methods such as a direct heating using dry and hot air and an indirect heating from a heat source through a partition may be used. Examples of the direct heating are a dry heating by an air stream and a dry heating by means of spraying while those of the indirect heating are a dry heating by means of a drum, etc.

The cyclopentenone in the heat-treated product used in the present invention can be collected using anticancer action, antibacterial action, apoptosis-inducing action, etc. as an index. With regard to a collecting means, any of known purifying and isolating means such as chemical methods and physical methods may be used. Thus, purifying methods which have been known already such as gel filtration, fractionating using a molecular weight fractionating membrane, extraction with solvent, fractional distillation, various chromatographic methods using ion-exchange resin or of a normal phase or a reversed phase, etc. may be jointly used whereby the cyclopentenone produced in the heat-treated substance can be collected.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated and the cyclopentenone is extracted with chloroform from the concentrate whereupon the cyclopentenone in the heat-treated substance is isolated.

Alternatively, the above-mentioned heat-treated glucuronic acid is treated with a column of ion-exchange resin, preferably that of anionic ion-exchange resin, and the non-adsorbed fraction is collected whereupon the cyclopentenone is purified. In another alternative, the above-mentioned heat-treated glucuronic acid is treated with a column of active carbon, the non-adsorbed fraction is removed and the column is washed and eluted with hydrophilic organic solvent such as aqueous solution of ethanol (preferably, aqueous solution of ethanol of 40% or higher concentration) whereupon the purified cyclopentenone is obtained. When those methods are combined, the cyclopentenone of a high purity can be obtained.

When the isolated cyclopentenone is subjected to an optical resolution, (−)-4,5-dihydroxy-2-cyclopenten-1-one and (+)-4, 5- dihydroxy-2-cyclopenten-1-one of the present invention can be obtained. It goes without saying that the cyclopentenone obtained by a synthetic method can be subjected to an optical resolution by the present invention as well.

Separation of the optically active substances can be conducted by subjecting the racemic mixture to mechanical resolution, preferential crystallization, resolution by crystallization as diastereomer salts or as inclusion compounds, dynamic resolution using enzymes or microorganism, resolution by means of chromatography, etc.

Gas chromatography, liquid chromatography, thin layer chromatography, etc. may be used in the case of a resolution by chromatography and a chiral stationary phase which is suitable for each of them may be used.

A method using a chiral stationary phase, a method using a chiral eluate, separation as a diastereomer, etc. may be used in an optical resolution by liquid chromatography.

A stationary phase of an amide type, that of a urea type, that of a ligand exchange type, polysaccharide-polysaccharide derivative stationary phase, protein stationary phase, polymethacrylic acid ester stationary phase, polymethacrylamide stationary phase, etc. may be used as a chiral stationary phase.

With regard to an eluting liquid, that of a hexane type, an alcohol type, an aqueous (buffer) type, etc. may be suitably used taking the combination with the above-mentioned stationary phase into consideration.

The method for the manufacture of the cyclopentenone used in the present invention may be any method. Thus, the cyclopentenone may be manufactured by the method disclosed in the present invention or by a chemical synthetic method [Carbohydrate Research, volume 247, pages 217–222 (1993); Helvetica Chimica Acta, volume 55, pages 2838–2844 (1972)] and trans- and cis- compounds of the cyclopentenone are used in the present invention. Needless to say, optically active substances of the cyclopentenone obtained by the chemical synthetic method are covered by the optically active substance of the present invention. Further, the cyclopentenone which is produced in the heat-treated substance of at least one selected from uronic acid, uronic acid derivative(s), a saccharide compound containing uronic acid and/or uronic acid derivative(s) and a substance which contains a saccharide compound containing uronic acid and/or uronic acid derivative(s) as well as purified product and optically active substance thereof may be used as well.

The cyclopentenone and its optically active substance show a cell growth suppressing action and anticancer action to cancer cells such as human promyelocytic leukemia cells HL-60, human acute lymphoblastic leukemia cells MOLT-3, pulmonary cancer cells A-549, SV40-transformed pulmonary cancer cells WI-38VA13, hepatoma cells Hep G2, colic cancer cells HCT 116, human colic cancer cells SW 480, human colic cancer cells WiDr, stomach cancer cells AGS and myeloma cells. Thus, the cyclopentenone and its optically active substance can be used as effective components of anticancer agent. They have an apoptosis-inducing action to those cancer cells too. Mechanism of the action for inhibiting the cancer cell growth of the cyclopentenone of the present invention and its optically active substance does not limit the scope of the present invention at all and, for example, an apoptosis inducing action to cancer cells is covered by the present invention.

When the cyclopentenone and/or its optically active substance having anticancer action are/is used as effective ingredient and made into a pharmaceutical preparation by compounding with known pharmaceutical carriers, it is now possible to prepare an anticancer agent. Generally, the cyclopentenone and/or its optically active substance are/is compounded with a pharmaceutically acceptable liquid or solid carrier and, if necessary, solvent, dispersing agent, emulsifier, buffer, stabilizer, filler, binder, disintegrating agent, lubricant, etc. are added thereto to give an anticancer agent which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethylcellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where the cyclopentenone and/or its optically active substance which are/is effective ingredient(s) of the present invention are/is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The anticancer agent of the present invention is administered by an appropriate route depending upon the form of the preparation. There is no particular limitation for the method of administration as well and it may be administered by oral use, external use and injection. Injection is administered, for example, intravenously, intramuscularly, subcutaneously, intracutaneously, etc. while preparations for external use include suppositories, etc.

Dose as an anticancer agent is appropriately decided by its form of preparation, method of administration, purpose of use and age, body weight and symptom of the patient to be treated with and it is not constant but, usually, the amount of the cyclopentenone and/or its optically active substance contained in the preparation is from 0.1 $\mu$g to 200 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The cyclopentenone and/or its optically active substance have/has an anticancer action and, at low concentrations, they/it show(s) an ability of inducing the differentiation of cancer cells whereby they/it are/is useful as a differentiation inducer (a decancerizing agent) for cancer cells. An inducer for cancer cell differentiation containing the cyclopentenone and/or its optically active substance as an effective ingredient can be made into pharmaceutical preparations in accordance with the above-mentioned method for anticancer agents and can be administered by the method similar to that for anticancer agents.

Dose as an inducer for cancer cell differentiation is appropriately decided by its form of preparation, method of administration, purpose of use and age, body weight and symptom of the patient to be treated with and it is not constant but, usually, the amount of the cyclopentenone and/or its optically active substance contained in the preparation is from 0.1 $\mu$g to 100 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis.

The inducer for cancer cell differentiation of the present invention can be used in a method for induction of cancer cell differentiation. Thus, when the cyclopentenone and/or its optically active substance are/is used as an effective ingredient, it is possible to differentiate the cancer cells and such a method is useful for elucidation of mechanism for induction of cancer cell differentiation, for screening of the differentiation inducers, etc.

When the cyclopentenone and/or its optically active substance are/is used as effective ingredient and made into a pharmaceutical preparation by compounding with known pharmaceutical carriers, it is now possible to prepare an antibacterial agent of the present invention. Generally, the cyclopentenone and/or its optically active substance are/is compounded with a pharmaceutically acceptable liquid or solid carrier and, if necessary, solvent, dispersing agent, emulsifier, buffer, stabilizer, filler, binder, disintegrating agent, lubricant, etc. are added thereto to give a solid preparation such as tablets, granules, diluted powders, powders, capsules, etc. or a liquid preparation such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethylcellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where the cyclopentenone and/or its optically active substance which are/is effective ingredients of the present invention are/is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The antibacterial agent of the present invention is administered by an appropriate route depending upon the form of the preparation. There is no particular limitation for the method of administration as well and it may be administered by oral use, external use and injection. Injection is administered, for example, intravenously, intramuscularly, subcutaneously, intracutaneously, etc. while preparations for external use include suppositories, etc.

Dose as an antibacterial agent is appropriately decided by its form of preparation, method of administration, purpose of use and age, body weight and symptom of the patient to be treated with and it is not constant but, usually, the amount of the cyclopentenone and/or its optically active substance contained in the preparation is from 10 $\mu$g to 20 mg/kg per day (for adults). Of course, the dose may vary depending upon various conditions and, therefore, the dose less than above may be sufficient in some cases while, in other cases, the dose more than above may be necessary. The pharmaceutical agent of the present invention can be directly administered orally and, in addition, it can be added to any food and beverage so that the agent can be taken on a routine basis. In addition, a substance that contains the cyclopentenone and/or its optically active substance may be used as materials for antibacterial food and beverage. Further, it may be used together with ethanol, glycine, sodium acetate, ascorbic acid, glycerol fatty acid esters, salt, EDTA and other antibiotic substances.

The antibacterial agent of the present invention containing the cyclopentenone and/or its optically active substance as effective ingredient may be used as an antiseptic agent for improving the preservability of food or beverage. In addition, the cyclopentenone and/or its optically active substance are/is added to food or beverage whereby they/it may be used in a method for making food or beverage antiseptic.

The form of the antibacterial agent containing the cyclopentenone an/or its optically active substance when it is added to food or beverage may be any of liquid, paste, powder, flakes, granules, etc. When an easy operation or the use by mixing with other additives are taken into consideration, it is preferred to make the agent powdery, flaky or granular by drying. With regard to the method for drying, commonly-used one such as spray drying, drum drying, shelf drying, vacuum drying, freeze drying, etc. may be used.

Amount of the cyclopentenone and/or its optically active substance to be added to food or beverage may vary depending upon the type of the food or beverage and the amount meeting with the object may be added.

One method of using the antibacterial agent of the present invention is that where the agent is added to food or to beverage by an appropriate method. There is no particular limitation for a method of addition but that will do ultimately if the cyclopentenone and/or its optically active substance are/is contained in food or beverage by any means. Accordingly, in the use of the antibacterial agent of the present invention, the term "addition" covers all methods whereby the cyclopentenone and/or its optically active substance are/is made to contain in food or beverage. Although the common method is to add them/it during the manufacturing steps of the food or beverage, a method where the food is dipped in a solution containing the cyclopentenone and/or its optically active substance may be used as well. It is also possible to conduct a method of adding it to the food together with a method of dipping the food in the solution. Examples of the food which is suitable for a dipping method are the food which does not lose its shape even in water such as fish or livestock meat paste (e.g., kamaboko [boiled fish paste] and Vienna sausage), noodles (e.g., boiled noodle) and frozen product of fish, shellfish and shrimp before freezing.

When the antibacterial agent of the present invention is used as an antiseptic agent, preservability of food or beverage can be further improved. In the case of frozen food and frozen dessert, growth of contaminated microorganisms in the processing step before freezing can be suppressed whereby a very favorable result in terms of hygiene can be obtained. The antibacterial agent of the present invention is effective to both gram-positive and gram-negative bacteria and is very effective, for example, to drug-resistant bacteria such as methicillin-resistant *Staphylococcus aureus* and bacteria which cause food poisoning such as Salmonella, enterotoxin-producing *Staphylococcus aureus, Bacillus cereus* of a vomiting type, *Bacillus cereus* of a diarrhea type and enterorrhagial *Escherichia coli* O157. It is also effective to hiochi bacteria. Further, it shows antibacterial action to microorganisms causing diseases which are caused by microorganisms such as *Legionella pneumophila* (a microorganism causing legionnaire's disease), *Vibrio parahaemolyticus* (a microorganism causing food poisoning), *Helicobacter pylori* (a microorganism causing ulcer), *Campylobacter jejuni* (a microorganism causing enterogastrisis), etc. including *Legionella pneumophila* (ATCC 33153), *Vibrio parahaemolyticus* (ATCC 17802), *Helicobacter pylori* (NCTC 11637), *Campylobacter jejuni* (ATCC 29428), etc. It is also effective to microorganisms such as yeast and fungi. The antiseptic agent containing the cyclopentenone and/or its optically active substance derived from natural food is particularly highly useful as a natural preventive agent for food poisoning and as a sterilizing agent. Incidentally, sterilization of clothing, bed sheet, etc. can be conducted using the antibacterial agent of the present invention and, when the antibacterial agent of the present invention is sprinkled or when wiping-off with the antibacterial agent of the present invention is conducted, it is possible to sterilize (both to remove and to kill the bacteria) the object to be sterilized. For example, when it is added to water for air-conditioning of office buildings, legionnaire's disease can be prevented.

The antibacterial agent of the present invention shows an antibacterial activity to bacteria for dental caries and those for periodontal disease and an intraoral preparations containing the antibacterial agent of the present invention can be offered. The form of the intraoral preparation may be a known one such as liquid or paste. An example of the intraoral preparation is a dentifrice. The dentifrice may be in a known form such as liquid, paste or powder. There is no particular limitation for the amount of the cyclopentenone and/or its optically active substance in the dentifrice and, if an effective concentration to the bacteria for dental caries and for periodontal disease is contained therein, that will be enough. Known additives such as moisturizing agents, surface-active agents, binders, perfumes, sweetening agents, etc. may be added to the dentifrice. With regard to the effective ingredient of the dentifrice of the present invention, the cyclopentenone-containing substances such as heat-treated vegetables, fruits, etc. may be used as well and an intraoral preparation containing such a heat-treated product which contains the cyclopentenone such as dentifrice may be included in the coverage of the present invention as well.

It is possible to offer antibacterial cosmetics using the antibacterial agent of the present invention. Examples of the cosmetics of the present invention are in the forms of basic cosmetics such as cream, milky lotion, lotion, face-washing material and pack; make-up cosmetics such as lipstick and foundation; body soap; and soap containing an effective amount of the cyclopentenone and/or its optically active substance. This is useful to hair as well and can be made into the hair care products including hair products such as hair tonic, hair liquid, hair set lotion, hair blowing preparation, hair cream and hair coat; and hair toiletry products such as shampoo, rinse and hair treatment. Usually, its amount in the cosmetics is about $10^{-3}$ to 10 parts (by weight, hereinafter this is used in the same meaning) or, preferably $10^{-2}$ to 1 part, of the cyclopentenone and/or its optically active substance in 100 parts of the cosmetic preparation. With regard to other ingredients, those which have been commonly compounded with cosmetics may be used. The cosmetic product of the present invention effectively acts to microorganisms causing atopic dermatitis as well and it shows significant effect to improvement and prevention of atopic dermatitis.

It is also possible to offer a bathing agent using the antibacterial agent of the present invention. The bathing agent of the present invention may be made into a form of powder, granules, solid, liquid, etc. containing the effective amount of the cyclopentenone and/or its optically active substance. The compounding amount to the bathing agent is usually about 10–100 parts (by weight; this is used in the same meaning as hereinafter) or, preferably 20–90 parts, of the cyclopentenone and/or its optically active substance in 100 parts of the bathing agent. About 5–25 grams of the bathing agent prepared as such is usually added to 200 liters of hot water. With regard to other ingredients for the bathing agent, those which have been commonly compounded therewith may be used. The bathing agent of the present invention effectively acts to microorganisms causing atopic dermatitis as well and it shows significant effect to improvement and prevention of atopic dermatitis. It is effective to exterminate the causing microorganism from the bathroom.

As such, the present invention offers an antibacterial agent which is useful as pharmaceuticals, cosmetics and bathing agent. Further, food or beverage containing the cyclopentenone, etc. is very useful for improvement and/or prevention of food poisoning, enterogastrisis, etc.

The apoptosis inducer of the present invention contains the apoptosis-inducing cyclopentenone and/or its optically active substance as effective ingredient(s). It can be made into pharmaceutical preparations by the same manner as in the above-mentioned case of anticancer agents and is administered by the means the same as in the anticancer agents.

The dose as the apoptosis inducers is not particularly specified but may be appropriately determined depending upon the dosage form, administration method, purpose of the use and the age, body weight, conditions, etc. of the patient to whom the inducer is administered. Usually, however, the amount of the cyclopentenone and/or its optically active substance contained in the preparation for an adult is 0.1 $\mu$g–100 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well.

Unlike necrosis which is a pathogenic death of cells, apoptosis is believed to be a death which is initially integrated in the gene of the cell itself. Thus, the gene which programs the apoptosis is activated by certain external or internal causes whereby programmed death gene protein is biosynthesized based upon said gene and then the cell itself is decomposed and dead by the resulting programmed death protein.

The apoptosis inducer of the present invention is quite useful since it is capable of expressing such apoptosis in desired tissues and cells and able to exclude the unnecessary or the pathogenic cells from living organisms in a natural state.

The apoptosis inducer of the present invention can be used in a method for the induction of apoptosis. Thus, when the cyclopentenone and/or its optically active substance are/is used as effective ingredient(s), it is possible to induce apoptosis and said method is useful, for example, for elucidation of a mechanism for apoptosis induction and for screening of apoptosis inducers and apoptosis induction inhibitors.

There is no particular limitation for the antibacterial food or beverage of the present invention and its examples are processed agricultural and forest products, processed livestock products, processed fishery products, etc. such as processed cereals (for example, processed wheat flour, processed starch, processed premix, noodles, macaroni, bread, bean paste, soba [buckwheat noodles], fu [wheat-gluten bread], biifun [Chinese noodles made of rice flour], harusame [sticks of bean jelly] and packed rice cake), processed fat/oil (for example, plastic fat/oil, oil for deep frying, salad oil, mayonnaise and dressing), processed soybeans (for example, tofu [soybean curd], miso [soybean paste] and natto [fermented soybeans]), processed meat products (for example, ham, bacon, pressed ham and sausage), fishery products (frozen fish paste, kamaboko [boiled fish paste], chikuwa [a kind of fish paste product], hampen [cake of pounded fish], satsuma-age [fried fish balls], tsumire [steamed fish balls], suji [boiled raw fish paste], fish meat ham, sausage, dried bonito, processed fish egg products, canned fishery products and tsukudani [food boiled down in soy sauce]), milk product (for example, crude milk, cream, yoghurt, butter, cheese, condensed milk, powdery milk and ice cream), processed vegetable and fruit products (for example, pastes, jams, pickles, fruit beverages, vegetable beverages and mixed beverages), confectioneries (for example, chocolate, biscuit, bun, cake, mochigashi [rice ball cake] and rice crackers), alcoholic beverages (for example, sake [Japanese rice wine], Chinese wines, wine, whisky, shochu [Japanese distilled liquor], vodka, brandy, gin, ram, beer, refreshing alcoholic drinks, fruit wine and liquors), table luxuries (for example, green tea, tea, oolong tea, coffee, refreshment beverage and lactic acid beverage), seasoning (for example, soy sauce, Wooster sauce, vinegar and mirin (sweetened Japanese rice wine), canned, bottled or bagged food (for example, boiled rice assorted with seasoned beef, kamameshi [boiled rice placed in a small kettle], sekihan [festive red rice], curried rice and other already-cooked food products), semi-dried or concentrated food (for example, liver paste and other spreads, soup for soba and udon [both being typical Japanese noodles] and concentrated soup), dried food (for examples, instant noodles, instant curry, instant coffee, powdery juice, powdery soup, instant soy paste soup, retort food, retort beverage and retort soup), frozen food (for example, frozen sukiyaki, chawanmushi [pot-steamed hotchpotch], kabayaki [grilled eel], hamburg steak, Chinese shao-mai, gyoza [fried dumpling stuffed with minced pork], various sticks and fruit cocktails), solid food products, liquid food products (for example, soup) and spices.

There is no particular limitation for the method of manufacturing the food and beverage of the present invention but cooking, processing and commonly-used manufacturing methods for food and beverage may be applied provided that the cyclopentenone and/or its optically active substance are/is contained in the resulting food or beverage.

Cooking and processing are to be conducted in such a manner that the cyclopentenone and/or its optically active substance are/is contained in the heat-treated product of a material selected from (a) uronic acid or uronic acid derivative(s), (b) a saccharide compound containing uronic acid and/or uronic acid derivative(s) and (c) a substance which contains a saccharide compound containing uronic acid and/or uronic acid derivative(s).

Thus, before, during or after cooking/processing, the heat-treated product of a material selected from (a) uronic acid or uronic acid derivative(s), (b) a saccharide compound containing uronic acid and/or uronic acid derivative(s) and (c) a substance which contains a saccharide compound containing uronic acid and/or uronic acid derivative(s) that contains cyclopentenone and/or its optically active substance may be added or, alternatively, cooked/processed product or a material thereof is added to the heat-treated product of a material selected from (a) uronic acid or uronic acid derivative(s), (b) a saccharide compound containing uronic acid and/or uronic acid derivative(s) and (c) a substance which contains a saccharide compound containing uronic acid and/or uronic acid derivative (s) that contains cyclopentenone and/or its optically active substance whereby the cyclopentenone and/or its optically active substance in said heated-treated substance can be diluted.

Then, in the manufacture of food or beverage, a heating treatment may be conducted during any of the steps whereby the cyclopentenone and/or its optically active substance may be made to contain in the heat-treated substance or, alternatively, a heat-treated substance which contains the cyclopentenone and/or its optically active substance may be added thereto. It is also possible that food, beverage or a material thereof is added to a heat-treated substance containing the cyclopentenone and/or its optically active substance so that the cyclopentenone and/or its optically active substance in said heat-treated substance may be diluted. Addition may be conducted either at one time or dividedly in several times. Thus, food or beverage showing novel physiological action can be manufactured easily and conveniently. Incidentally, food or beverage containing the cyclopentenone and/or its optically active substance in the heat-treated substance produced during the manufacture as constituting components after adding (a) uronic acid or uronic acid derivative(s), (b) a saccharide compound containing uronic acid and/or uronic acid derivative(s) and (c) a substance which contains a saccharide compound containing uronic acid and/or uronic acid derivative (s) during the manufacture is also covered by the present invention. In case where any of the steps is applied, food or beverage wherein the cyclopentenone and/or its optically active substance is contained, added and/or diluted is defined as the food or beverage of the present invention.

There is no particular limitation for the content of the cyclopentenone and/or its optically active substance having physiological action contained in the food but the content may be appropriately selected in view of organoleptic property and physiological activity such as anticancer and antibacterial actions. However, for example, the content of the cyclopentenone and/or its optically active substance in 100 parts of food is $5 \times 10^{-6}$ part or more and, in view of organoleptic property and physiological action as food, it is preferably from $10^{-5}$ to 5 parts or, more preferably, from $10^{-4}$ to 2 parts.

There is no particular limitation for the content of the cyclopentenone having a physiological action in the beverage but the content may be appropriately selected in view of organoleptic property and physiological activity such as anticancer and antibacterial properties. However, for example, the content of the cyclopentenone in 100 parts of beverage is $5 \times 10^{-6}$ part or more and, in view of organoleptic property and physiological action of the beverage, it is preferably from $10^{-5}$ to 5 parts or, more preferably, from $10^{-4}$ to 2 parts.

There is no particular limitation for the shape of the food or beverage of the present invention so far as the cyclopentenone and/or its optically active substance having physiological actions such as anticancer and antibacterial activities are/is contained therein, added thereto and/or diluted thereby. Thus, the shape includes orally takable ones such as tablets, granules, capsules, gel and sol.

As mentioned hereinabove, the cyclopentenone and/or its optically active substance used in the present invention can be manufactured in a low cost and, due to various physiological functions thereof, they/it can be used as additive(s) to food or beverage whereby it is now possible to easily give various physiological functions, antibacterial activity, apoptosis-inducing action, anticancer action, etc. to food and beverage. Thus, the cyclopentenone and/or its optically active substance of the present invention are/is quite useful as additive(s) to food or beverage.

The cyclopentenone and/or its optically active substance used in the present invention may be manufactured by any method. Thus, they/it may be manufactured by a method disclosed in the present invention or by a chemical synthetic method. Thus, all of food, beverage, antibacterial agents, anticancer agents, inducers for cancer cell differentiation and apoptosis inducers containing the cyclopentenone and/or its optically active substance are covered by the present invention. Further, all methods for inducing the cancer cell differentiation and for inducing apoptosis using the cyclopentenone and/or its optically active substance as effective ingredient(s) are covered by the present invention as well.

The cyclopentenone and/or its optically active substance do(es) not show toxicity to mice by oral administration of 100 mg/kg.

As fully mentioned hereinabove, the cyclopentenone and/or its optically active substance can be manufactured easily in a low cost and, due to various physiological functions thereof, they/it are/is quite useful compound(s) in broad areas including pharmaceuticals and food.

EXAMPLES

The present invention will now be further illustrated by way of the following examples which, however, do not limit the scope of the present invention thereto. Incidentally, the terms % and "part(s)" used in the examples are those by weight unless otherwise mentioned.

Example 1

(1) Commercially available pectin made from apple was dissolved in water to make its concentration 1% and the solution was placed in an egg-plant flask equipped with a reflux condenser and heated on an oil bath kept at 110–120° C. for 18, 42 and 66 hours. Temperature of the pectin solution during heating was 100–102° C.

The pectin solution was centrifuged to remove the precipitate and the supernatant liquid was diluted 3- and 10-fold with water to prepare samples. Then the heat-treated product was adjusted to pH 7.0 with NaOH and its cell growth inhibiting action to human promyelogenous leukemia cells (HL-60 cells) (ATCC CCL-240) was measured by an MTT method which will be mentioned below.

Thus, 10 µl of the diluted sample and 100 µl of RPMI 1640 medium (manufactured by Nissui) containing 5000 HL-60 cells incubated at 37° C. in an RPMI 1640 medium containing 10% of fetal calf serum (manufactured by Gibco) treated at 56° C. for 30 minutes were added to wells of a 96-well microtiter plate, incubated in the presence of 5% of carbon dioxide gas at 37° C. for 48 hours, 10 µl of phosphate buffered saline containing 5 mg/ml of 3-(4,5-dimethylthiazol-2-yl)-2,5-diphenyltetrazolium bromide (MTT; manufactured by Sigma) was added, the mixture was incubated for additional four hours and the growth state of the cells was observed under microscope. Incidentally, 100 µl of 2-propanol containing 0.04 N HCl was added, the mixture was well stirred and the absorbance at 590 nm was measured and used as a degree of cell growth.

As a result, no viable cell was noted in a fraction to which 3-fold diluted solution of pectin heated for 18 hours and in fractions to which 3- and 10-fold diluted solution of pectin heated for 42 and 66 hours and, in such diluted concentrations, pectin which was heated at 100° C. showed an inhibiting activity to cell growth.

On the other hand, in the fraction to which 10-fold diluted solution of pectin heated for 18 hours, nearly all cells were living though, as compared with the water-added fraction used as a control, the absorbance at 590 nm was low.

(2) Methanol (200 μl) was added to 200 μl of pectin heated at 100° C. for 18–66 hours followed by mixing, the mixture was centrifuged and 200 μl of the supernatant liquid was concentrated to dryness in vacuo. This was dissolved in 10 μl of 50% aqueous solution of methanol, 1 μl of it was spotted on a silicagel 60 sheet $F_{254}$ (manufactured by Merck) and was developed with a developing solvent (the upper layer of a 3:1:1 mixture of butyl acetate, acetic acid and distilled water). The thin-layer silica gel after the development was dried, sprayed with a solution of $AgNO_3$—$NH_3$ (an equivolume mixture of 0.1 M $AgNO_3$ and 5 N $NH_3$) and heated to detect a spot. The result was that a spot near Rf=about 0.3 appeared in pectin heated for 18 hours, that an increase was noted in pectin heated for 42 hours as compared with pectin heated for 18 hours and that, in pectin heated for 66 hours, the amount was nearly same as in pectin heated for 42 hours.

(3) Methanol (1 ml) was added to 1 ml of pectin heated at 100 ° C. for 66 hours mentioned in Example 1 (1) followed by mixing and centrifuging to give a supernatant liquid. This was concentrated to dryness in vacuo and the residue was suspended in 100 μl of methanol. This suspension was centrifuged to remove insoluble matters, the supernatant liquid was spotted onto a silica gel 60 sheet $F_{254}$ and a development was conducted using a solvent mentioned in Example 1(2). A part of the thin layer was cut off and colored by a method of Example 1(2) to confirm the appearance of a spot at around Rf=about 0.3 and the silica gel part corresponding to this Rf value was scraped up from the uncolored thin layer.

The scraped silica gel was extracted with each 1 ml of methanol for three times and the extract was concentrated to dryness in vacuo to isolate a spot of Rf value of about 0.3. This dried substance was dissolved in 250 μl of water, the solution was 10-fold diluted further and 10 μl of the diluted solution was used as a sample for measuring the cell growth inhibiting activity to HL-60 cells by an MTT method mentioned in Example 1(1).

The result was that, in the wells to which water was added, most of the cells grew while, in the wells to which this diluted solution was added, no viable cell was noted. Thus, the inhibiting action of this scraped fraction to cancer cell growth was confirmed.

(4) Mass spectrometric analysis of the cancer cell growth inhibiting substance near Rf=0.3 isolated in Example 1(3) was conducted by a DX302 mass spectrometer (manufactured by Nippon Denshi). In addition, structure analysis was conducted by means of a nuclear magnetic resonance method (NMR) using heavy chloroform as solvent. The NMR apparatus used was JNM-A500 (manufactured by Nippon Denshi). The results are as follows.

FAB—MS m/z 115 $[M+H]^+$

Glycerol was used as a matrix.

$^1$H—NMR ($CDCl_3$): δ 4.20 (1H, d, J=2.4 Hz, 5-H), 4.83 (1H,m, 4-H), 6.30 (1H, dd, J=1.2, 6.1 Hz, 2-H), 7.48 (1H, dd, J=2.1, 6.1 Hz, 3-H).

Incidentally, the chemical shift value of the $^1$H—NMR was given in such a manner that the chemical shift value of $CHCl_3$ was 7.26 ppm.

Those values coincided with the data for trans-4,5-dihydroxy-2-cyclopenten-1-one reported by T. Ahmad, et al. in Carbohydrate Research, volume 247, pages 217–222 (1993).

FIG. 1 shows the mass spectrum in which the ordinate is a relative intensity (%) while the abscissa is m/z values.

Figure 2:
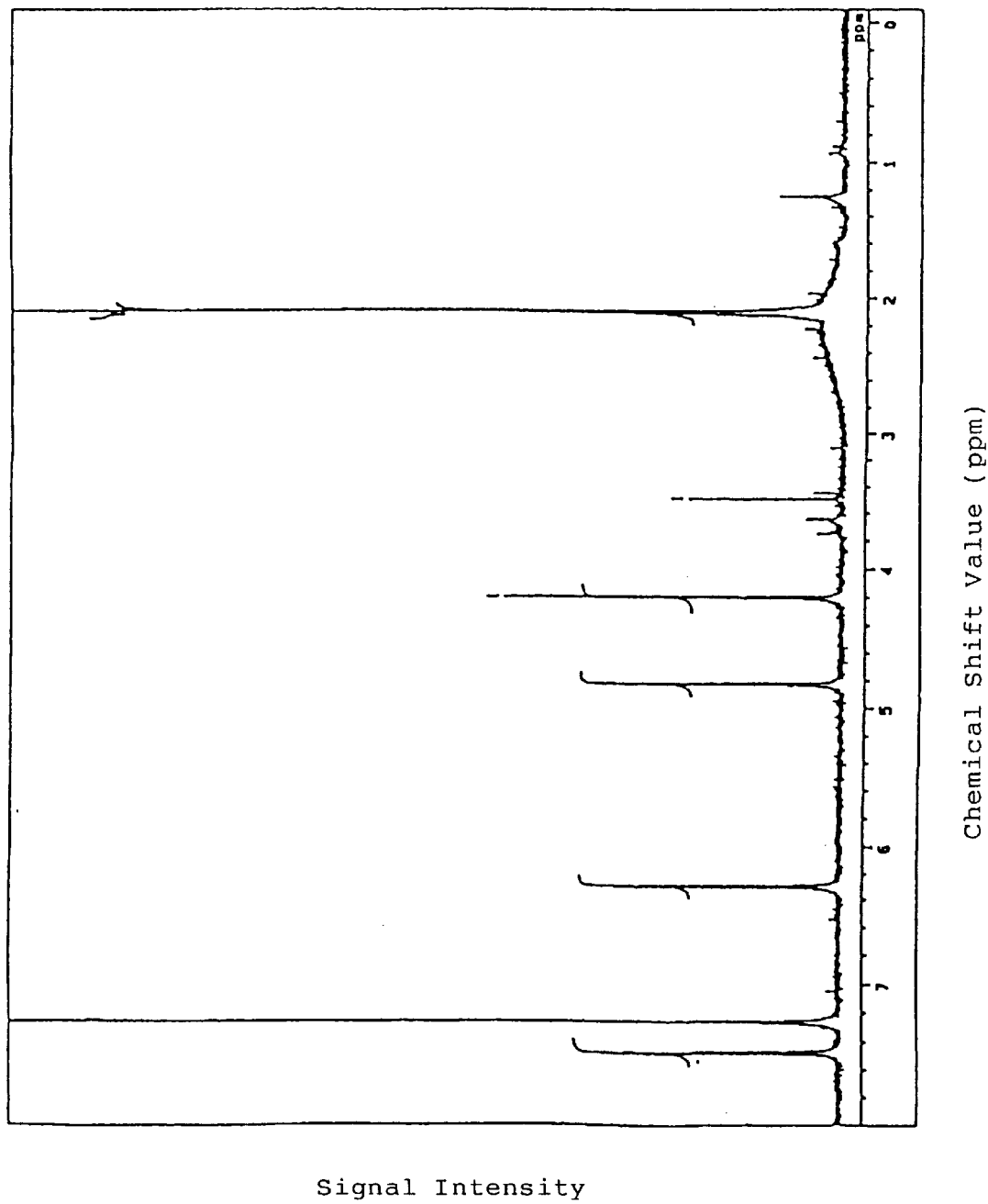
FIG. 2 shows a $^1$H—NMR spectrum of the cyclopentenone.

FIG. 2 shows the $^1$H—NMR spectrum in which the ordinate is a signal intensity while the abscissa is a chemical shift value (ppm).

Example 2

(1) Alginic acid (non-swelling; manufactured by Wako Pure Chemicals) (25 g) was suspended in 475 ml of water, heated at 121° C. for two hours and centrifuged, the resulting supernatant liquid was filtered through a membrane filter of 0.22 μm and the filtrate was concentrated in vacuo until it became 20 ml. This was mixed with 180 ml of ethanol, allowed to stand at- 20° C. for one hour and centrifuged to give a supernatant fluid. The supernatant liquid was concentrated in vacuo to 20 ml, 180 ml of acetonitrile was added, the mixture was centrifuged, the resulting supernatant was concentrated in vacuo to 20 ml, the concentrate was again centrifuged after adding 180 ml of acetonitrile and the supernatant liquid was concentrated to 15 ml in vacuo. The concentrated solution (4 ml) was concentrated in vacuo to about 400 μl and stirred with an equivolume upper layer of a 3:2:2 mixture of butyl acetate, acetic acid and water and centrifugal supernatant liquid was collected. This was repeated to give 8 ml of extract.

The extract (4 ml) was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute with a pressure of 0.18 kg/cm$^2$ using a compressor. Fractionation was conducted to make a volume of one fraction 6–7 ml and a part of each fraction was analyzed by a thin layer chromatography whereupon cyclopentenone of a high purity was contained in 31st to 35th fractions to afford 35 mg of cyclopentenone.

The fraction was separated by means of a normal phase HPLC using a PALPACK type S column and, when a detection was conducted by an ultraviolet absorption of 215 nm, the purity was found to be 95.8%.

(2) The cyclopentenone prepared in Example 2-(1) was used for preparing aqueous solutions of the cyclopentenone in the concentrations of 2.86 mM, 955 μM, 318 μM, 106 μM, 35 μM, 12 μM and 0.18 μM. Then said heat-treated substance was adjusted to pH 7.0 with NaOH and the apoptosis-inducing activity to HL-60 cells was measured as follows.

HL-60 cells which were incubated at 37° C. in an RPMI 1640 medium containing 10% of fetal bovine serum treated at 56° C. for 30 minutes were suspended in an RPMI 1640 medium containing 10% of fetal bovine serum to make the concentration 5.8×10$^4$ cells/1.35 ml.

To 1.35 ml of this suspension was added 0.15 ml of the above-mentioned cyclopentenone solution and the mixture was incubated at 370° C. for 20 hours in the presence of 5% of carbon dioxide gas.

As a result, it was noted that, in the fractions (final concentration: 10.6 μM) to which 106 μM or higher of cyclopentenone was added after 20 hours from the incubation, viable cell numbers and cell viability decreased and that, in the fraction (final concentration: 3.5 μM) to which 35 μM of cyclopentenone was added, molecular weight of DNA became small and shape of the cells was changed (i.e. condensation of the nuclei, shrinkage of the cell and production of apoptic body) as a result of induction of apoptosis.

Figure 3:
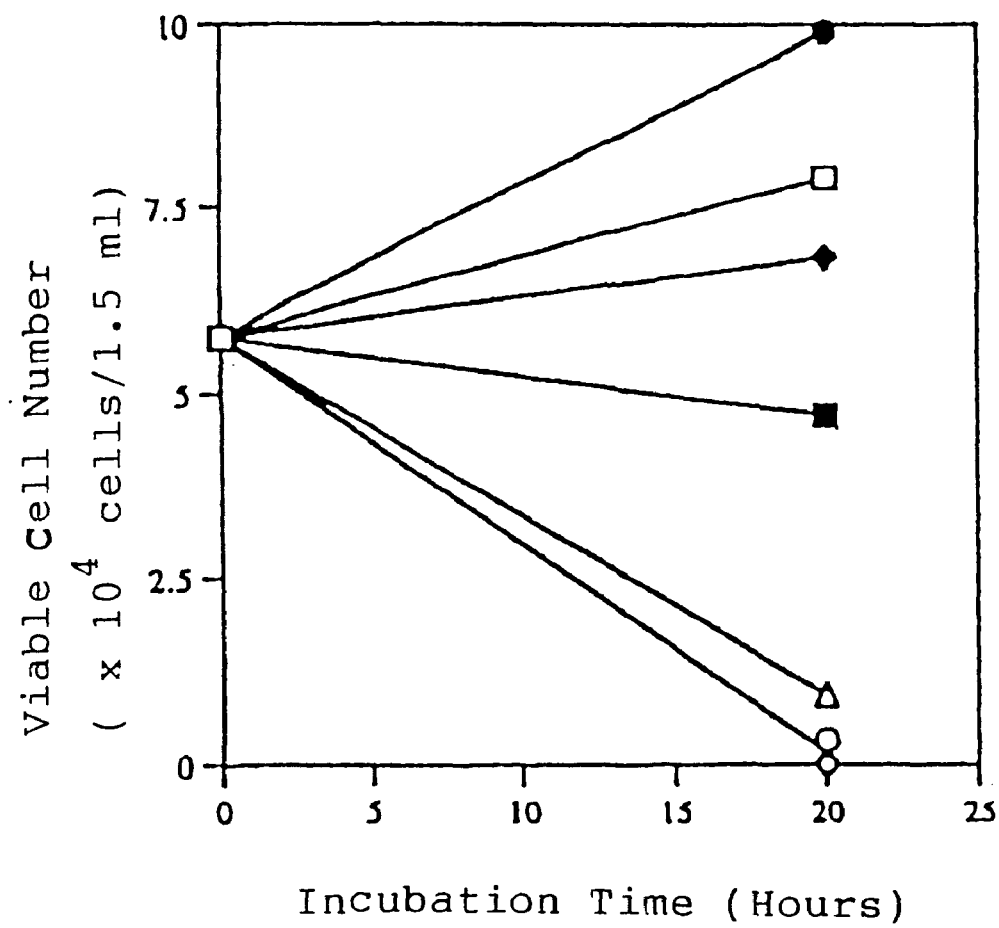
FIG. 3 shows an apoptosis-inducing action of the cyclopentenone prepared from the heated-treated products of alginic acid.

The results are shown in FIG. 3. Thus FIG. 3 shows the relation between the incubation time and viable cell number when cyclopentenone of various concentrations is added to the culture of HL-60 cells wherein the abscissa is an incubation time (hours) while the ordinate shows a viable cell number (×10⁴/1.5 ml) in the culture.

In FIG. 3, an open square is a fraction to which no sample was added (control); an open rhomb is a fraction to which 2.86 mM cyclopentenone was added; an open circle is a fraction to which 955 $\mu$M cyclopentenone was added; an open triangle is a fraction to which 318 $\mu$M cyclopentenone was added; a black square is a fraction to which 106 $\mu$M cyclopentenone was added; a black rhomb is a fraction to which 35 $\mu$M cyclopentenone was added; and a black circle is a fraction to which 12 $\mu$M cyclopentenone was added.

Example 3

(1) D-Glucuroic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute with a pressure of 0.2 kg/cm² using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a PALPACK type S column and, when a detection was conducted by an ultraviolet absorption of 215 nm, the purity was found to be 98%.

(2) A mass spectrometric analysis of the above cyclopentenone was conducted using a mass spectrometer DX302. Further, a structure analysis was conducted by means of an NMR using heavy chloroform as solvent. The nuclear magnetic resonance apparatus used was JNM-A 500. Specific rotation was measured by a DIP-370 polarimeter (manufactured by Nippon Bunko); ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu). Results of the mass spectrometric analysis and the NMR were the same as those in Example 1-(4). Others were as follows.

Optical rotation: $[\alpha]_D^{20}$ 0° (c=1.3, water)

IR (KBr method): absorptions were noted at 3400, 1715, 1630, 1115, 1060, 1025 cm⁻¹.

UV: $\lambda_{max}$ 215 nm (water)

Figure 4:
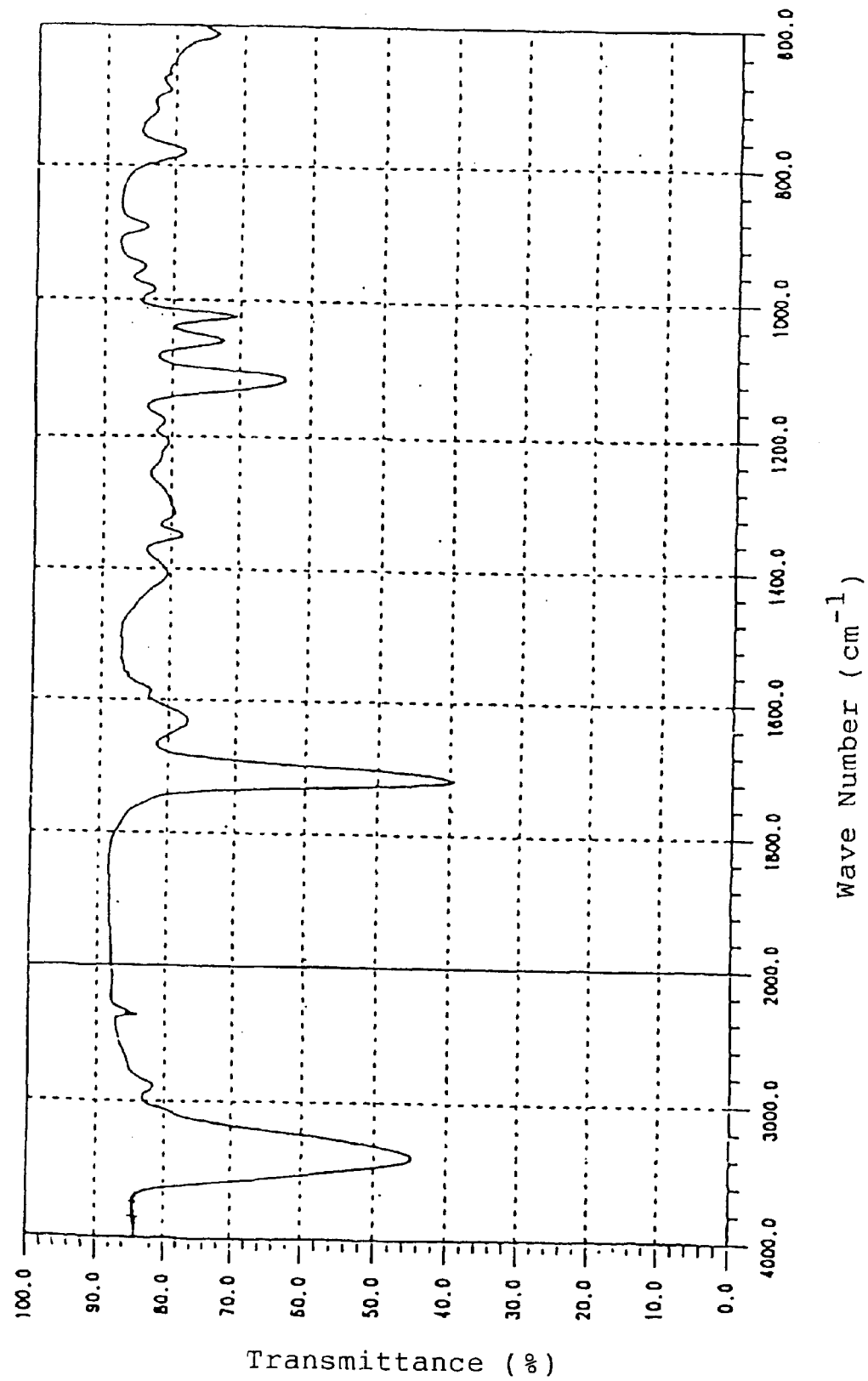
FIG. 4 shows an IR absorption spectrum of the cyclopentenone.

FIG. 4 shows the IR spectrum wherein the abscissa is a wave number (cm⁻¹) while the ordinate is a transmittance.

Figure 5:
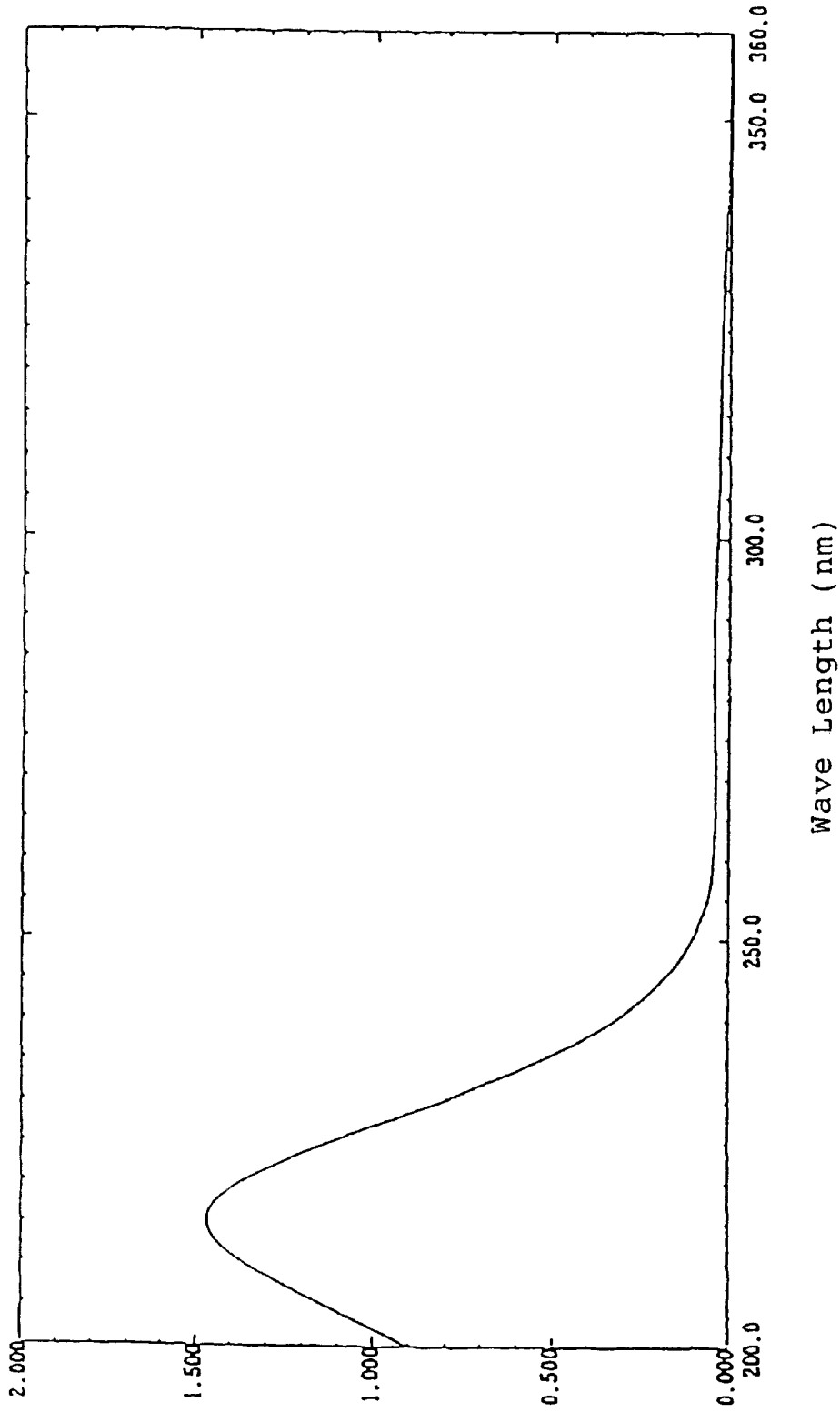
FIG. 5 shows a UV absorption spectrum of the cyclopentenone.

FIG. 5 shows the UV absorption spectrum wherein the abscissa is a wave length (nm) while the ordinate is an absorbance.

Example 4

A 1% aqueous solution of D-glucuronic acid (G 5269; manufactured by Sigma) was heated at 121° C. for four hours and adjusted to pH 7 with 1 N NaOH. The sample (5 ml) was applied to a HiTrap Q column (5 ml; manufactured by Pharmacia) equilibrated with water and the column was washed with 25 ml of water. A fraction (5 ml) which was firstly eluted form the column was called P0 fraction; the second fraction (5 ml) was called P1 fraction; the third one (10 ml) was called P2 fraction; and the last one (10 ml) was called P3 fraction. After that, the column was eluted with 25 ml of 0.5 M acetic acid. A fraction (5 ml) which was firstly eluted form the column was called E0 fraction; the second fraction (5 ml) was called E1 fraction; the third one (5 ml) was called E2 fraction; and the last one (10 ml) was called E3 fraction.

A part of each of the fractions was analyzed by means of a thin layer chromatography and it was found that the cyclopentenone was contained in the P1 fraction and was quantitatively recovered in this fraction. In the P1 fraction, there was neither unreacted glucuronic acid nor reductic acid which was a reaction product, which were contained prior to the purification by a HiTrap Q column.

Example 5

(1) Purified cyclopentenone sample mentioned in Example 3-(1) was dissolved in water to make the concentration 0.67 mg/ml. In the meanwhile, n-octacosane (manufactured by Nacalai Tesque) was dissolved in n-hexane (manufactured by Nacalai Tesque) to make the concentration 1 mg/ml. To each of five tubes, each 100 $\mu$l (100 $\mu$g) of n-octacosane solution was added while, with regard to aqueous solution of cyclopentenone, each of 15 $\mu$l (10 $\mu$g), 45 $\mu$l (30 $\mu$g), 90 $\mu$l (60 $\mu$g), 135 $\mu$l (90 $\mu$g) and 180 $\mu$l (120 $\mu$g) was added. The tubes were dried in vacuo and to each was added 100 $\mu$l of trimethylsilylation solution [a 4:1:1 mixed solution of N,O-bis(trimethylsilyl)-acetamide (manufactured by Nacalai Tesque), trimethylchlorosilane (manufactured by G. L. Science) and pyridine (manufactured by Pierce)] to make the content completely dissolved.

A 2% OV17 Uniport HP 60/80 mesh (manufactured by G. L. Science) was filled in a glass column of 2.1 m length and 3.2 mm diameter (manufactured by Shimadzu) and subjected to burned in a carrier gas (N₂) at a flow rate of 20 ml/minute for fifteen hours using a gas chromatographic apparatus GC-7AG (manufactured by Shimadzu).

Each of the above-mentioned trimethylsilylated sample (1 $\mu$l) was applied in this gas chromatographic system. Analyzing conditions are as given below.

Carrier gas: N₂

Flow rate: 50 ml/minute

Temperature at the inlet: 280° C.

Initial temperature: 80° C., four minutes

Rising rate of the temperature: 8° C./minute

Final temperature: 270 ° C.

Detection: by hydrogen flame ionization detector

The result was that a single peak of cyclopentenone was detected at the retention time of about 9.7 minutes while that of n-octacosane was detected at the retention time of about 26.7 minutes. Areas of the peaks obtained at that time are as given below.

| Amount of Cyclopentenone | Peak Area of Cyclopentenone (a) | Peak Area of n-Octacosane (b) | Ratio of (a)/(b) |
| --- | --- | --- | --- |
| 10 µg | 19,981 | 285,798 | 0.06991 |
| 30 µg | 90,980 | 285,398 | 0.3188 |
| 60 µg | 174,284 | 251,439 | 0.6931 |
| 90 µg | 272,524 | 256,356 | 1.063 |
| 120 µg | 368,573 | 255,545 | 1.442 |

Figure 6:
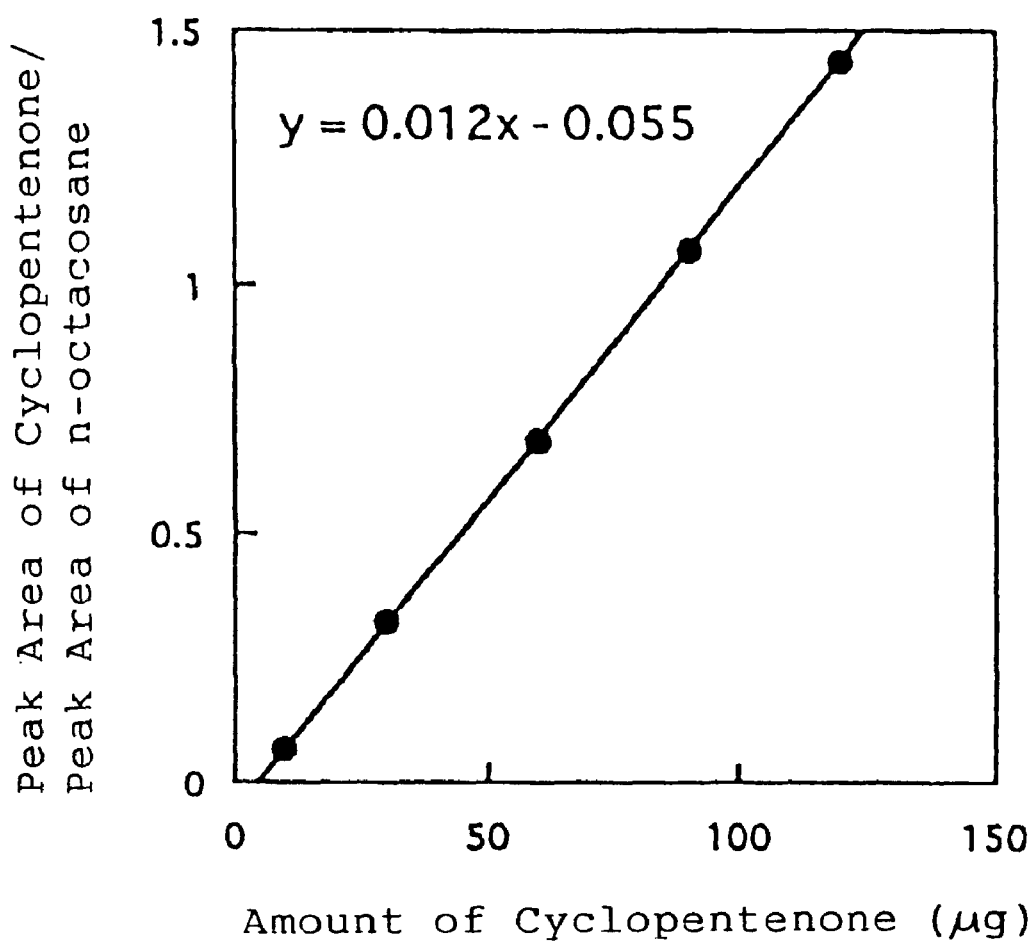
FIG. 6 shows a working curve of the cyclopentenone.

When the relation between the amount of the cyclopentenone and "[peak area (a) of cyclopentenone]/[peak area (b) of n-octacosane]" obtained as such is expressed by a graph, that is as shown in FIG. 6. Thus, FIG. 6 is a graph which shows a working curve of the cyclopentenone wherein the ordinate is a ratio of peak area of cyclopentenone to that of n-octacosane while the abscissa is the amount of cyclopentenone in µg.

Thus, the amount of cyclopentenone can be determined when 100 µg of n-octacosane is added to a sample wherein the amount of cyclopentenone is unknown, dried in vacuo, trimethylsilylated and analyzed by means of a gas chromatography according to the above-mentioned method and the ratio (y) of "peak area of cyclopentenone" to "peak area of n-octacosane" is calculated.

Figure 7:
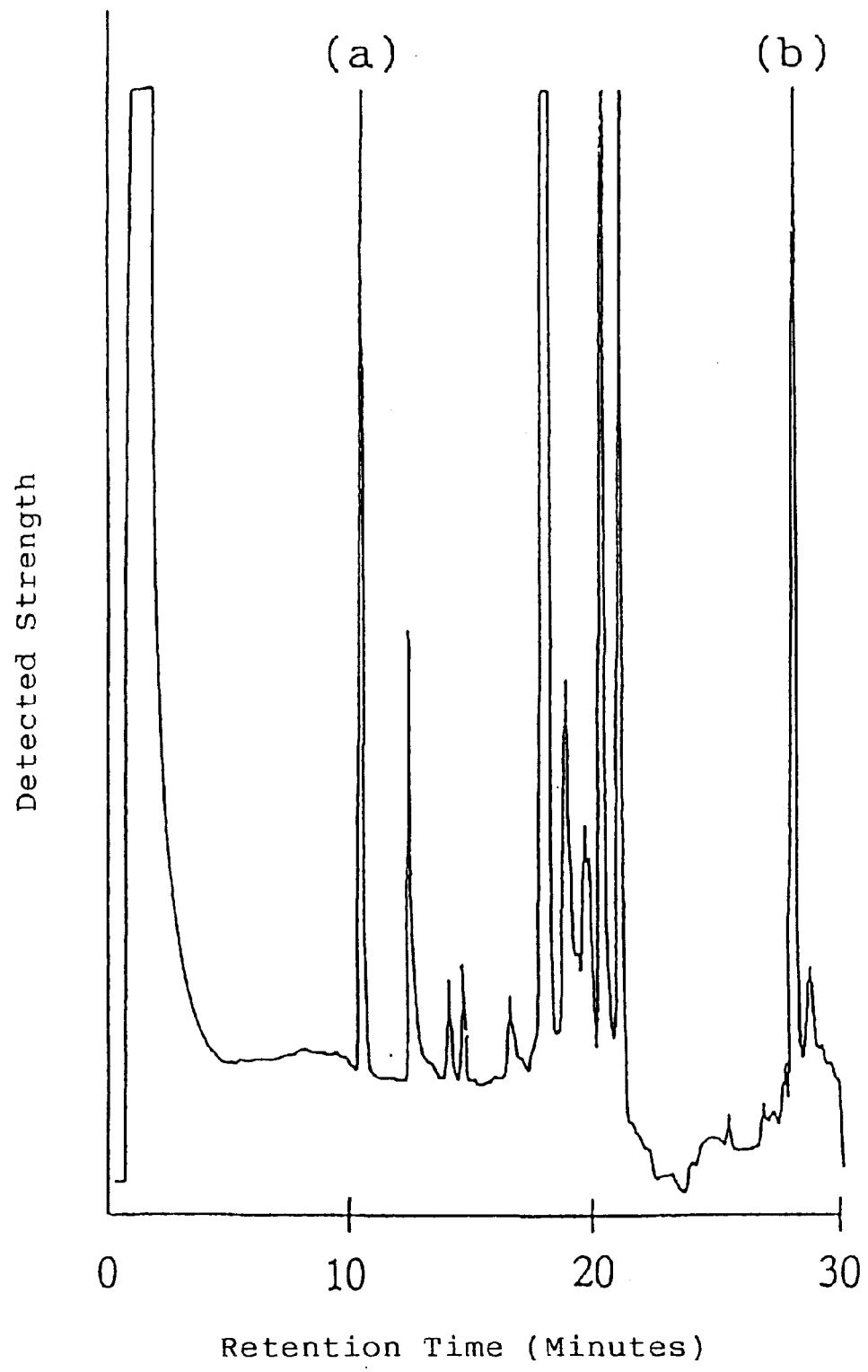
FIG. 7 shows the gas chromatographic results of the heat-treated products of glucuronic acid.

(2) An aqueous solution of glucuronic acid (manufactured by Nacalai Tesque) prepared in a concentration of 1% (by weight) was heated at 120° C. for four hours under pressure in an autoclave. This (100 µl) (corresponding to 1 mg of glucuronic acid) was placed in a tube, 100 µg of n-octacosane was added thereto and the mixture was dried in vacuo and trimethylsilylated. This was subjected to a gas chromatographic analysis by the same method as given above to give a pattern as shown in FIG. 7. Thus FIG. 7 shows a gas chromatographic result of the heat-treated glucuronic acid wherein the ordinate is a detected strength while the abscissa is a retention time (minutes). Each single peak was detected for cyclopentenone at the retention time of about 10.2 minutes [peak (a)] and for n-octacosane at the retention time of about 27.8 minutes [peak (b)].

The results are as shown below and the rate of conversion by heating treatment of glucuronic acid to cyclopentenone was about 15% in terms of moles.

Peak area (a) of cyclopentenone: 203,794

Peak area (b) of n-octacosane: 305,444

(a)/(b): 0.6672

Amount of cyclopentenone (µg): 88.4

Example 6

Commercially available glucuronolactone (manufactured by Merck; code no. 100282) was dissolved in water to make its concentration 1% and heated at 121° C. for 0.5 hour, 1 hour, 2 hours, 4 hours or 16 hours. The heat-treated solution was trimethylsilylated according to a method mentioned in Example 5-(1) and subjected to a gas chromatographic analysis.

Results of the analysis are as follows.

| Heating Time (hours) | Amount of Cyclopentenone (µg/100 µl) | Converting Ratio (%; in moles) |
| --- | --- | --- |
| 0.5 | 9.28 | 1.43 |
| 1 | 21.0 | 3.26 |
| 2 | 52.8 | 8.15 |

-continued

| Heating Time (hours) | Amount of Cyclopentenone (µg/100 µl) | Converting Ratio (%; in moles) |
| --- | --- | --- |
| 4 | 119 | 18.3 |
| 16 | 132 | 20.4 |

The result was that the converting ratio of glucuronolactone into cyclopentenone by a heating treatment in terms of moles was about 20%.

Further, pure cyclopentenone was obtained from a solution of glucuronolactone heated for 16 hours by a method mentioned in Example 3-(1).

Example 7

Water (100 ml) was added to 100 g of commercially available cabbage followed by crushing with a mixer. This was made to react with 5 ml of proteinase K (20 mg/ml; #9033 manufactured by Takara Shuzo) at 50° C. for one hour and filtered and the precipitate was washed with 1.5 liters of water. Water (100 ml) was added to the washed precipitate and the resulting suspension of pH 6.5 was heated at 121° C. for two hours followed by filtering to give a filtrate of pH 4.7. The filtrate was concentrated in vacuo to 14 ml, mixed with 36 ml of methanol and centrifuged at 4000×g for ten minutes and the resulting supernatant liquid was concentrated in vacuo to give 3.5 ml of a concentrated liquid.

Amount of the cyclopentenone contained in this concentrated liquid was determined by a method mentioned in Example 5-(1) and found to be 24.9 µg. When treatment with proteinase K and removal of protein by washing with water were not conducted after crushing by a mixer but just heated as it was, no cyclopentenone was produced. From this result, it is now clear that 0.87 mg of cyclopentenone was produced when 100 g of cabbage was treated with proteinase K, washed with water to remove protein and heated at the above conditions.

After that, cyclopentenone was isolated in a pure form from this concentrated liquid by a method of Example 3-(1).

Example 8

(1) Pectinase (8.1 units/mg protein; P9932 manufactured by Sigma) was added in an amount of 1.36 units, 0.68 unit or 0.14 unit to 8 ml of a 1% aqueous solution of pectin (from apple; manufactured by Wako Pure Chemicals) and allowed to stand at 25° C. for overnight. HCl was added to (1) the enzymatic reaction product and (2) supernatant liquid of the enzymatic reaction product after centrifugation to adjust to pH 3 followed by heating at 121° C. for four hours to give heat-treated products. The cyclopentenone contained in the heat-treated product was tri-methylsilylated by a method of Example 5-(1) and the amount of the cyclopentenone in the heat-treated product was determined by means of a gas chromatography.

The results are given in Table 1.

TABLE 1

| Amount of Pectinase Added | Converting Ratio (% in terms of wt.) | |
| --- | --- | --- |
| (units/80 mg pectin) | (1) | (2) |
| 1.36 | 4.46 | 4.75 |
| 0.68 | 4.52 | 4.62 |

TABLE 1-continued

| Amount of Pectinase Added | Converting Ratio (% in terms of wt.) | |
|---|---|---|
| (units/80 mg pectin) | (1) | (2) |
| 0.14 | 3.39 | 3.43 |
| 0 | 2.71 | 2.73 |

The result shows that, when pectin was hydrolyzed with pectinase and then heated, production of the cyclopentenone increased by 25–75% as compared with the case where only heating was conducted.

(2) Alginic acid (non-swelling; manufactured by Wako Pure Chemicals) (1 g) was suspended or dissolved in 100 ml of either (1) 0.1 N HCl or (2) 0.1 M $Na_2CO_3$, heated at 95° C. for 15 hours and adjusted to pH 2.7 by adding powdery $Na_2CO_3$ to (1) or 6 N HCl to (2). In the meanwhile, 1 g of alginic acid was suspended in (3) 100 ml of water (resulting pH: 2.7) or in (4) 100 ml of 0.1 M $Na_2CO_3$ followed by adjusting to pH 2.7 with 6 N HCl. Amount of the cyclopentenone contained in the (1)–(4) heated at 121° C. for four hours (hereinafter, called samples (1) to (4)) was determined by the following method.

Insoluble matters contained in the samples (1)–(4) were removed by means of centrifugation and 10 μl of the supernatant liquid was analyzed by means of a gel filtration HPLC using a TSK gel G 2000 PW column (7.5 mm×30 cm; manufactured by Tosoh). Water was used as a mobile phase, flow rate and column temperature were made 1 ml/minute and 40° C., respectively and detection was conducted using an absorption at 215 nm. Pure cyclopentenone mentioned in Example 3-(1) was used as a standard substance and 2-cyclopenten-1-one (manufactured by Aldrich) was used as an internal standard substance.

As a result thereof, it was found that the samples (1), (2), (3) and (4) contained 414 μg/ml, 279 μg/ml, 289 μg/ml and 296 μg/ml of cyclopentenone, respectively. Thus, as compared with the sample (3) heated at 121° C. for four hours, the case where heating in 0.1 N HCl at 95° C. for 15 hours was conducted before heating at 121° C. for four hours gave 1.43-fold cyclopentenone.

Pure cyclopentenone was prepared from each of those samples by a method mentioned in Example 3-(1).

(3) Water (120 ml) was added to 50 g of commercially available okara (lees of bean curd) and shaken at room temperature and solid was removed by centrifugation and filtration. To 50 ml of the filtrate was added 1 N $H_2SO_4$ to adjust to pH 2 followed by heating at 121° C. for four hours to give a sample (5).

Acetone (300 ml) was added to 100 g of okara, stirred and filtered to give 55 g of residue. The residue (27.5 g) was washed with one liter of water, water was added to make 150 ml, pH was adjusted to 2 with 1 N $H_2SO_4$ and the mixture was heated at 121° C. for four hours to give a sample (6).

The remaining residue (27.5 g) for the acetone treatment was suspended in 200 ml of water and made to react with 500 μl of proteinase K (20 mg/ml; manufactured by Takara Shuzo) at 50° C. for two hours. The reaction product was washed with one liter of water, made into 180 ml by adding water thereto, adjusted to pH 2 with 1 N $H_2SO_4$ and heated at 121° C. for four hours to give a sample (7).

Each of the samples (5)–(7) were filtered, the filtrate was concentrated in vacuo to 10 ml, 4-fold by volume of acetone was added and the mixture was centrifuged to give a supernatant fluid. The supernatant fluid was further concentrated in vacuo whereupon 5.5 ml, 3.8 ml and 3.0 ml of concentrated liquids were obtained from the samples (5), (6) and (7), respectively. Amount of the cyclopentenone contained in the concentrated liquids was determined by a method which will be mentioned in Example 8-(2).

The results were that, starting from 50 g of okara, 0.54 mg, 2.79 mg and 3.98 mg of the cyclopentenone was obtained from the samples (5), (6) and (7), respectively. Incidentally, in any of the samples during the preparation of the samples (5)–(7) prior to heating at 121 ° C. for four hours, no cyclopentenone was contained. Accordingly, as a result of removal of protein by treating with proteinase, production of the cyclopentenone increased by about 40%.

Pure cyclopentenone was prepared from each of the samples (5)–(7) by a method mentioned in Example 3-(1).

Okara (50 g) was suspended in 200 ml of water, adjusted to pH 1.5 with 6 N HCl and heated at 50° C. for three hours. This was adjusted to pH 5.0 with NaOH and filtered to give a filtrate. The filtrate was adjusted to pH 2.05 with 6 N HCl and heated at 121° C. for four hours to give a sample (8). Amount of the cyclopentenone contained in the sample (8) was determined by a method mentioned in Example 8-(2).

The result was that 5.0 mg of the cyclopentenone was produced from 50 g of okara. Incidentally, in a filtrate before heating at 121° C. for four hours, no cyclopentenone was contained.

(4) Commercially available apple fiber (dry powder; manufactured by Nichiro) was treated as follows.

Apple fiber (0.5 g) was suspended in 50 ml of water, heated at 121° C. for four hours and centrifuged to give 37 ml of supernatant liquid which will be called a sample (9).

Apple fiber (5 g) was suspended in 50 ml of water, heated at 121° C. for four hours and centrifuged to give 20 ml of supernatant liquid which will be called a sample (10).

Apple fiber (5 g) was suspended in 50 ml of water, shaken at room temperature for two hours, centrifuged and the supernatant liquid was heated at 121° C. for four hours and centrifuged to give 25 ml of supernatant liquid which will be called a sample (11).

The precipitate obtained by centrifugation after shaking at room temperature for two hours in the preparation of the sample (11) was suspended in 50 ml of water, heated at 121° C. for four hours and centrifuged to give 31 ml of supernatant liquid which will be called a sample (12).

Amount of the cyclopentenone contained in the samples (9)–(12) was determined by a method mentioned in Example 8-(2).

The result was that the samples (9), (10), (11) and (12) contained 14.8 μg/ml, 76.3 μg/ml, 54.0 μg/ml and 34.2 μg/ml of the cyclopentenone, respectively. The sample prior to heating at 121° C. for four hours for the manufacture of the sample (9) contained no cyclopentenone. Accordingly, 1 g of apple fiber produced 1.09 mg, 0.305 mg, 0.270 mg and 0.212 mg of the cyclopentenone by a manufacturing methods for samples (9), (10), (11) and (12), respectively.

Pure cyclopentenone was prepared from each of the samples (9)–(12) by a method mentioned in Example 3-(1).

Example 9

Commercially available leaves (2 g) of sencha (green tea of middle grade), hojicha (roasted tea), oolong tea or tea was crushed by a mixer with 100 ml of water, adjusted to pH 3 with 1 N sulfuric acid and heated at 121° C. for 16 hours. Amount of the cyclopentenone contained in the heat-treated products was determined by means of a gel filtration HPLC mentioned in Example 8-(2). The result was that 0.19 mM, 0.28 mM, 0.34 mM and 0.12 mM of the cyclopentenone were produced from sencha, hojicha, oolong tea and tea, respectively. Those materials were subjected to a dry heating treatment during the manufacturing stage and the cyclopentenone was efficiently produced.

Example 10

Pectin (manufactured by Wako Pure Chemicals; code 167-00542), alginic acid (non-swelling; manufactured by Wako Pure Chemicals; code 011-13341), D-α-galacturonic acid (manufactured by Nacalai Tesque; code 165-18) or D-glucuroic acid (manufactured by Nacalai Tesque; code 169- 28) was dissolved in distilled water to prepare a 1% solution. With regard to pectin, a solution dissolved in 1N aqueous solution of acetic acid was prepared as well.

pH of the 1% aqueous solution of pectin was 3.4; pH of a 1% solution of pectin in acetic acid was 2.6; pH of an aqueous solution of galacturonic acid prior to heating was 2.5; pH of an aqueous solution of glucuronic acid prior to heating was 2.4; and pH of an aqueous solution of alginic acid prior to heating was 3.3.

Those 1% solutions were heated at 121° C. for 2, 4 or 16 hours. Each of the heat-treated solutions was adjusted to pH 7 with NaOH and sterilized with a filter of 0.22 μm to prepare a sample for determination of produced amount of the cyclopentenone.

The cyclopentenone was spotted on a silica gel sheet 60F$_{254}$ (manufactured by Merck) and developed with a developer (upper layer of a 3:1:1 mixture of butyl acetate, acetic acid and distilled water) and the thin layer of silica gel after completion of the development was dried, sprayed with an AgNO$_3$-NH$_3$ solution (a mixture of same amounts of 0.1M AgNO$_3$ and 5N NH$_3$) and heated whereupon the cyclopentenone was detected as a spot at around Rf=0.3.

The above-prepared "sample for determination of produced amount of the cyclopentenone" was diluted to an extent of 2-, 5-, 10-, 20-, 50- and 100-fold and the resulting diluted solutions were subjected to a TLC by the above manner. Incidentally, the produced amount of the cyclopentenone from a 2-fold diluted solution of a heat-treated product of a 1% aqueous solution of pectin for two hours was defined as one unit and the amount of the cyclopentenone produced in each of the heat-treated products was determined. The results are shown in Table 2.

In each of the samples, production of the cyclopentenone increased as the increase in the heating time and, in the heat-treated products of aqueous solution of galacturonic acid, 1 unit and 5 units of the cyclopentenone were produced after 30 minutes and one hour, respectively while, in the heat-treated products of aqueous solution of glucuroic acid, 5 units and 10 units of the cyclopentenone were produced after 30 minutes and one hour, respectively.

TABLE 2

| Sample to be Heated | Heating Time (hrs) | pH before Heating | pH after Heating | pH after Adjustment | Produced Cyclopentenone Unit |
|---|---|---|---|---|---|
| 1% Aq Soln of Pectin | 2 | 3.4 | 3.3 | 7.0 | 1 |
| | 4 | 3.4 | 3.2 | 7.2 | 5 |
| | 16 | 3.4 | 3.5 | 7.0 | 10 |
| 1% Soln of Pectin in | 2 | 2.6 | 2.7 | 7.0 | 1 |
| | 4 | 2.6 | 2.6 | 7.2 | 2 |

TABLE 2-continued

| Sample to be Heated | Heating Time (hrs) | pH before Heating | pH after Heating | pH after Adjustment | Produced Cyclopentenone Unit |
|---|---|---|---|---|---|
| Acetic Acid | 16 | 2.6 | 2.8 | 7.1 | 10 |
| 1% Aq Soln of Galacturonic Acid | 2 | 2.5 | 2.4 | 6.9 | 10 |
| | 4 | 2.5 | 2.4 | 6.8 | 25 |
| | 16 | 2.5 | 2.6 | 6.9 | 50 |
| 1% Aq Soln of Glucuronic Acid | 2 | 2.4 | 2.7 | 6.9 | 25 |
| | 4 | 2.4 | 2.6 | 7.0 | 50 |
| | 16 | 2.4 | 2.8 | 7.0 | 50 |
| 1% Aq Soln of Alginic Acid | 2 | 3.3 | 2.5 | 6.9 | 5 |
| | 4 | 3.3 | 2.7 | 7.0 | 5 |
| | 16 | 3.3 | 2.9 | 7.3 | 10 |

Example 11

(1) Commercially available glucuronolactone (manufactured by Merck; code no. 100282) was dissolved in water to prepare a 1% solution and it was heated at 121° C. for 0.5 hour, 1 hour, 2 hours, 4 hours or 16 hours. The heat-treated solutions were trimethylsilylated by a method of Example 5-(1) and the amount of the resulting cyclopentenone was analyzed by means of a gas chromatography.

Results of the measurement are given in Table 3.

TABLE 3

| Heating Time (hours) | Amount of Cyclopentenone (μg/100 μl) | Converting Rate (%) (calculated in moles) |
|---|---|---|
| 0.5 | 9.28 | 1.43 |
| 1 | 21.0 | 3.26 |
| 2 | 52.8 | 8.15 |
| 4 | 119 | 18.3 |
| 16 | 132 | 20.4 |

The result was that the converting rate of glucuronolactone to the cyclopentenone by heating for 16 hours was about 20% when calculated as moles.

The cyclopentenone was purified/isolated from the above solution prepared by heating glucuronolactone for 16 hours by a method mentioned in Example 3-(1).

(2) The above glucuronolactone was dissolved in water to prepare a solution of 1%, 2%, 5%, 10% or 20% followed by heating at 121° C. for four hours. This heat-treated solution was trimethylsilylated by the method mentioned in Example 5-(1) and the amount of the resulting cyclopentenone was determined by means of gas chromatography. The results are shown in Table 4.

TABLE 4

| Concn of Glucuronolactone (%) | Amount of the Cyclopentenone (μg/100 μl) | Converting Rate (%) (calculated as moles) |
|---|---|---|
| 0.1 | 15.1 | 23.2 |
| 1 | 99.2 | 15.3 |
| 3 | 229 | 11.8 |
| 5 | 365 | 11.3 |
| 10 | 455 | 7.03 |
| 20 | 592 | 4.58 |

The result was that, when a 0.1% aqueous solution of glucuronolactone was used, the converting rate of glucuronolactone upon heating to the cyclopentenone was about 23% when calculated as moles.

(3) The pH of the above 1% aqueous solution of glucuronolactone was adjusted to pH 1, 2, 3 or 4.5 by HCl or NaOH followed by heating at 121° C. for four hours. The heat-treated solution was trimethylsilylated by the method mentioned in Example 5-(1) and the amount of the resulting cyclopentenone was determined by means of gas chromatography. The results are shown in Table 5.

TABLE 5

| pH | Amount of the Cyclopentenone (μg/100 μl) | Converting Rate (%) (calculated as moles) |
|---|---|---|
| 1 | 7.85 | 1.21 |
| 2 | 15.9 | 2.46 |
| 3 | 108 | 16.7 |
| 4.5 | 125 | 19.3 |

The result was that, when pH was 4.5, the converting rate of glucuronolactone to the cyclopentenone by heating was about 19% when calculated as moles.

(4) The pH of 1% aqueous solution of galacturonic acid was adjusted to 1, 2, 3, 4, 5, 6 or 7 by HCl or NaOH followed by heating at 121° C. for four hours. The heat-treated solution was trimethylsilylated by a method mentioned in Example 5-(1) and the amount of the resulting cyclopentenone was determined by means of gas chromatography.

The results are shown in Table 6.

TABLE 6

| pH | Amount of the Cyclopentenone (μg/100 μl) | Converting Rate (%) (calculated as moles) |
|---|---|---|
| 1 | 16.6 | 2.83 |
| 2 | 66.6 | 11.3 |
| 3 | 42.7 | 7.27 |
| 4 | 7.36 | 1.25 |
| 5 | 5.47 | 0.931 |
| 6 | 5.45 | 0.927 |
| 7 | 0 | 0 |

The result was that, when pH was 2, the converting rate of glucuronic acid to the cyclopentenone by heating was about 11% when calculated as moles.

(5) A 1% aqueous suspension of alginic acid (non-swelling) was adjusted to pH 1, 2, 3 or 4 with HCl or NaOH. On the other hand, alginic acid (non-swelling) was dissolved to prepare a 1% solution in 0.1M acetate buffer followed by adjusting to pH 5 or in 0.1M phosphate buffer followed by adjusting to pH 6 or 7. The solutions were heated at 121° C. for four hours. Amount of the cyclopentenone contained in the heated solutions was determined by means of a gel filtration HPLC under the following conditions.

Column: TSK gel α-2500 (7.8×800 mm; manufactured by Tosoh)

Column temperature: 40° C.

Mobile phase: 0.01% aqueous solution of trifluoroacetic acid

Flow rate: 1 ml/minute

Detection: by means of absorbance at 215 nm

Pure cyclopentenone prepared in Example 3-(1) was used as a standard substance and the peak area of the cyclopentenone eluted at around 10.0 minutes was measured whereby concentration of the cyclopentenone was determined.

The results are shown in Table 7.

TABLE 7

| pH | pH After Heating | Concentration of the Cyclopentenone (μg/100 μl) | Converting Rate (%) (calculated as moles) |
|---|---|---|---|
| 1 | 1.07 | 0 | 0 |
| 2 | 1.98 | 0.536 | 0.611 |
| 3 | 2.76 | 2.00 | 2.28 |
| 4 | 4.01 | 1.05 | 1.20 |
| 5 | 5.02 | 0.167 | 0.190 |
| 6 | 5.95 | 0 | 0 |
| 7 | 6.90 | 0 | 0 |

The result was that, when pH was 3, the converting rate of alginic acid to the cyclopentenone by heating was about 2.3% when calculated as moles.

Example 12

Pomosin pectin type LM-13CG (manufactured by Hercules), alginic acid HFD (manufactured by Dainippon Pharmaceutical), D-glucuronic acid (manufactured by Nacalai Tesque) or glucuronolactone (manufactured by Merck) was dissolved or suspended in water to make the concentration 1% followed by heating at 30° C., 60° C., 95° C., 121° C. or 132° C. for 16 hours. The cyclopentenone in the heat-treated substance was trimethylsilylated by a method mentioned in Example 5-(1) and the amount of the cyclopentenone produced in the heat-treated substance was determined by means of gas chromatography. The results are shown in Table 8.

TABLE 8

| Uronic Acid Compound | Heating Temperature (° C.) | Amount of the Cyclopentenone Produced (μ/ml) |
|---|---|---|
| Pectin | 121 | 176 |
|  | 132 | 128 |
| Alginic acid | 121 | 466 |
|  | 132 | 75 |
| Glucuronic acid | 95 | 302 |
|  | 121 | 718 |
|  | 132 | 132 |
| Glucuronolactone | 95 | 274 |
|  | 121 | 781 |
|  | 132 | 161 |

Example 13

(1) Chondroitin sulfate A (manufactured by Seikagaku), chondroitin (sodium salt; manufactured by Seikagaku), dermatan sulfate (sodium salt; manufactured by Serbio), heparin (sodium salt; manufactured by Wako Pure Chemicals) or hyaluronic acid (manufactured by Seikagaku) was dissolved in water to prepare a 1% solution followed by adjusting to pH 3 with 1N HCl. These were heated at 121° C. for 4 or 16 hours to prepare a heat-treated solution.

(2) The heat-treated solution (100 μl) of chondroitin sulfate A, chondroitin, dermatan sulfate or heparin prepared in Example 13-(1) was mixed with a solution (1 mg/ml; 100 μl) of n-octacosane (manufactured by Nacalai Tesque) in n-hexane (manufactured by Nacalai Tesque) followed by drying in vacuo. To this was added 100 μl of the above trimethylsilylation solution to completely dissolve and the amount of the cyclopentenone in the heat-treated substance was determined by a method mentioned in Example 5-(1).

The results are shown in Table 9.

TABLE 9

| | Amount of the Cyclopentenone (μg/ 100 μl) in the Solution Heated for | |
|---|---|---|
| | 4 hours | 16 hours |
| Chondroitin sulfate A | 9.26 | 15.71 |
| Chondroitin | 7.47 | 9.11 |
| Dermatan sulfate | 32.81 | 47.60 |
| Heparin | 5.09 | 5.12 |

(3) The heated solution (100 μl) of hyaluronic acid was dried in vacuo, suspended in 10 μl of methanol and insoluble matters were removed by centrifugation. The supernatant liquid (1 μl) after centrifugation was spotted onto a sheet of silica gel 60F$_{254}$ (manufactured by Merck) and subjected to a thin layer chromatography (TLC) using an upper layer of a 3:2:2 mixture of butyl acetate, acetic acid and water as a developer. After the development, coloration was conducted by an orcinol-sulfate method and comparison was made with a spot of standard cyclopentenone. The result was that production of the cyclopentenone was noted in the heated product of hyaluronic acid for 4 hours and, in that for 16 hours, the increased amount was noted.

Example 14

Dermatan sulfate (1 g) was dissolved in 100 ml of water and the solution was adjusted to pH 3 with 1N HCl and heated at 121° C. for 16 hours to prepare a heat-treated solution. Then the cyclopentenone was purified from the heat-treated substance according to a method of Example 3-(1) to give 30 mg of pure cyclopentenone.

Example 15

(1) The purified/isolated cyclopentenone mentioned in Example 3-(1) was dissolved in water, 10 mM tris-HCl (pH 7) or 10 mM tris (pH 10) to make a concentration 25 mM, allowed to stand at room temperature or at 4° C. and analyzed by a TLC mentioned in Example 13-(3). The result was that, when dissolved in water or in 10 mM tris-HCl (pH 7), both solutions allowed to stand at room temperature and at 4° C. gave some decomposed matters after one month although mostly nondecomposed. In case of the solution which was dissolved in 10 mM tris (pH 10), a rapid decomposition was noted at room temperature and, when an analysis was conducted by a TLC immediately after dissolution, no spot for the cyclopentenone was noted.

When the cyclopentenone which was dissolved in water was heated at 121° C. for 30 minutes and analyzed by a TLC, some decomposed products were noted although most of the cyclopentenone was left nondecomposed.

(2) A 1% aqueous solution of D-glucuronic acid was heated at 121° C. for four hours and made into a sample where pH was unadjusted and another sample where pH was adjusted to 6.6 with NaOH. Each 1 ml of them was separated into some and stored at −20° C., 4° C. or 37° C. followed by trimethylsilylating by a method of Example 5-(1). After that, the amount of the cyclopentenone in the sample was determined by means of a gas chromatography.

Figure 8:
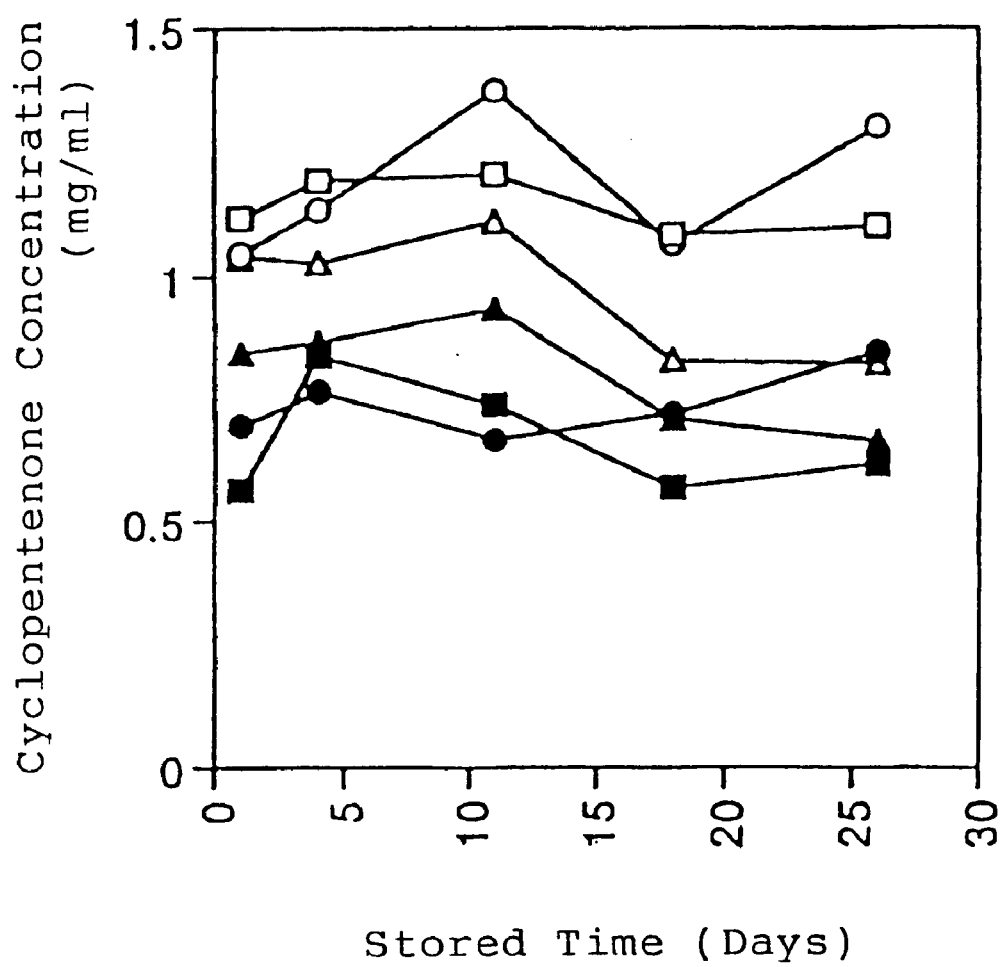
FIG. 8 shows a relationship between the storing time and the amount of the cyclopentenone.

The result after stored for 25 days was that, in case stored at 37° C., some decrease was noted in the amount of the cyclopentenone while, in case stored at 4° C. and at −20° C., the state was almost stable. Said result is shown in FIG. 8. Thus, FIG. 8 is a graph showing the relation between the storing time and the amount of the cyclopentenone wherein the abscissa is a stored time (days) and the ordinate shows the cyclopentenone concentration (mg/ml). In FIG. 8, open square shows the case where pH was unadjusted and stored at −20° C.; black square shows that case where pH was 6.66 and stored at −20° C.; open circle shows the case where pH was unadjusted and stored at 4° C.; black circle shows the case where pH was 6.66 and stored at 4° C.; open triangle shows the case where pH was unadjusted and stored at 37° C.; and black triangle shows the case where pH was 6.66 and stored at 37° C.

Example 16

(1) The purified/isolated cyclopentenone (113.9 mg) mentioned in Example 3-(1) was dissolved in 2.85 ml of ethanol. To this ethanolic solution was added 3.85 ml of hexane/ethanol (94/6) to prepare a cyclopentenone solution (17 mg/ml). This was filtered through a filter of 0.5 μm to prepare a sample solution for optical resolution HPLC.

This sample solution was subjected to an optical resolution HPLC, each of the fractions of the cyclopentenone in the earlier peak and the later peak was collected and evaporated to dryness in vacuo to give 43.2 mg of the cyclopentenone of the earlier peak and 43.0 mg of that of the later peak.

Conditions for Optical Resolution HPLC.

Columns: Chiral Pack AS (manufactured by Daicel) 2.0 cm×25.0 cm

Column temperature: 40° C.

Mobile phase: hexane/ethanol (94/6)

Flow rate: 14.0 ml/minute

Detection: UV 210 nm

Amount of the charged sample: 150 μl (2.55 mg)

Each of the cyclopentenones in both earlier and later peaks contains about 1% of enantiomer and, therefore, they were subjected to an optical resolution under the above-mentioned conditions again. As a result, 19.7 mg of the cyclopentenone containing no enantiomer was obtained from 30.0 mg of that of the earlier peak while, from 37.4 mg of that of the later peak, 27.7 mg of the cyclopentenone containing no enantiomer. Optical rotations of the cyclopentenones form the earlier and the later peaks obtained as such were $[\alpha]_D^{20}$ −105° (c=0.30, ethanol) and $[\alpha]_D^{20}$ +104° (c=0.53, ethanol), respectively. Thus, the earlier peak substance was (−)-trans-4,5-dihydroxy-2-cyclopenten-1-one [hereinafter, referred to as the (−)-cyclopentenone] and the later peak substance was (+)-trans-4,5-dihydroxy-2-cyclopenten-1-one [hereinafter, referred to as the (+)-cyclopentenone]. Incidentally, the optical rotation was measured by a polarimeter of a DIP-370 type (manufactured by Nippon Bunko) which was mentioned already.

Figure 9:
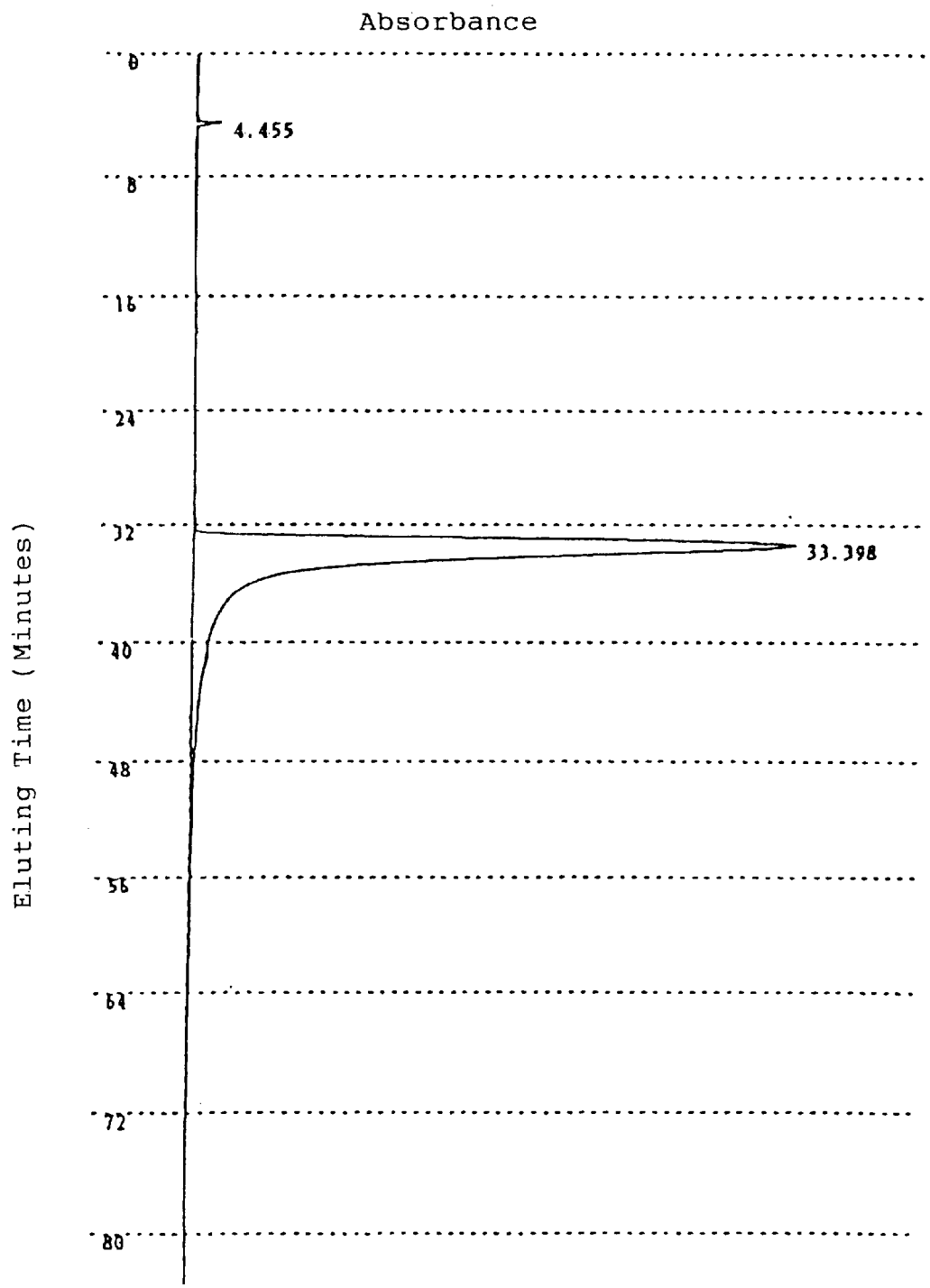
FIG. 9 shows an elution curve of (−)-4,5-dihydroxy-2-cyclopenten-1-one.
Figure 10:
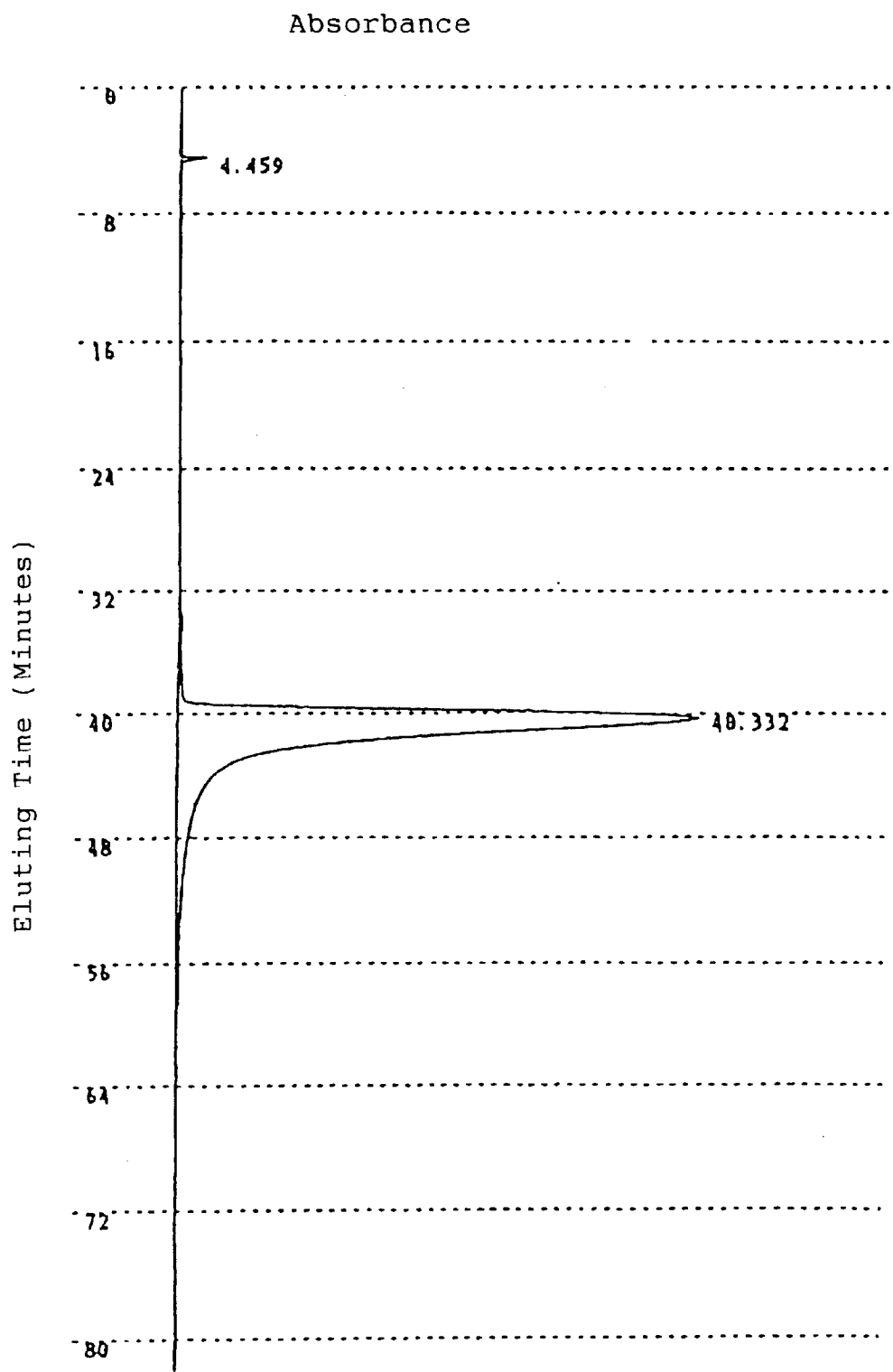
FIG. 10 shows an elution curve of (+)-4,5-dihydroxy-2-cyclopenten-1-one.

Eluting curves of the optical resolution HPLC of the (−)-cyclopentenone and the (+)-cyclopentenone are shown in FIG. 9 and FIG. 10, respectively. Thus, FIG. 9 is an eluting curve of the (−)-cyclopentenone where the ordinate shows an absorbance while the abscissa shows an eluting time (minutes). FIG. 10 is an eluting curve of the (+)-cyclopentenone where the ordinate shows an absorbance while the abscissa shows an eluting time (minutes).

Then each of (−)- and (+)-cyclopentenone was subjected to mass spectrometric analysis, structure analysis by nuclear magnetic resonance (NMR), measurement of UV absorption spectrum and measurement of infrared absorption analysis according to a method mentioned in Example 3-(2). The result was that both optically active substances show the same result as that of the cyclopentenone before the optical resolution.

Figure 11:
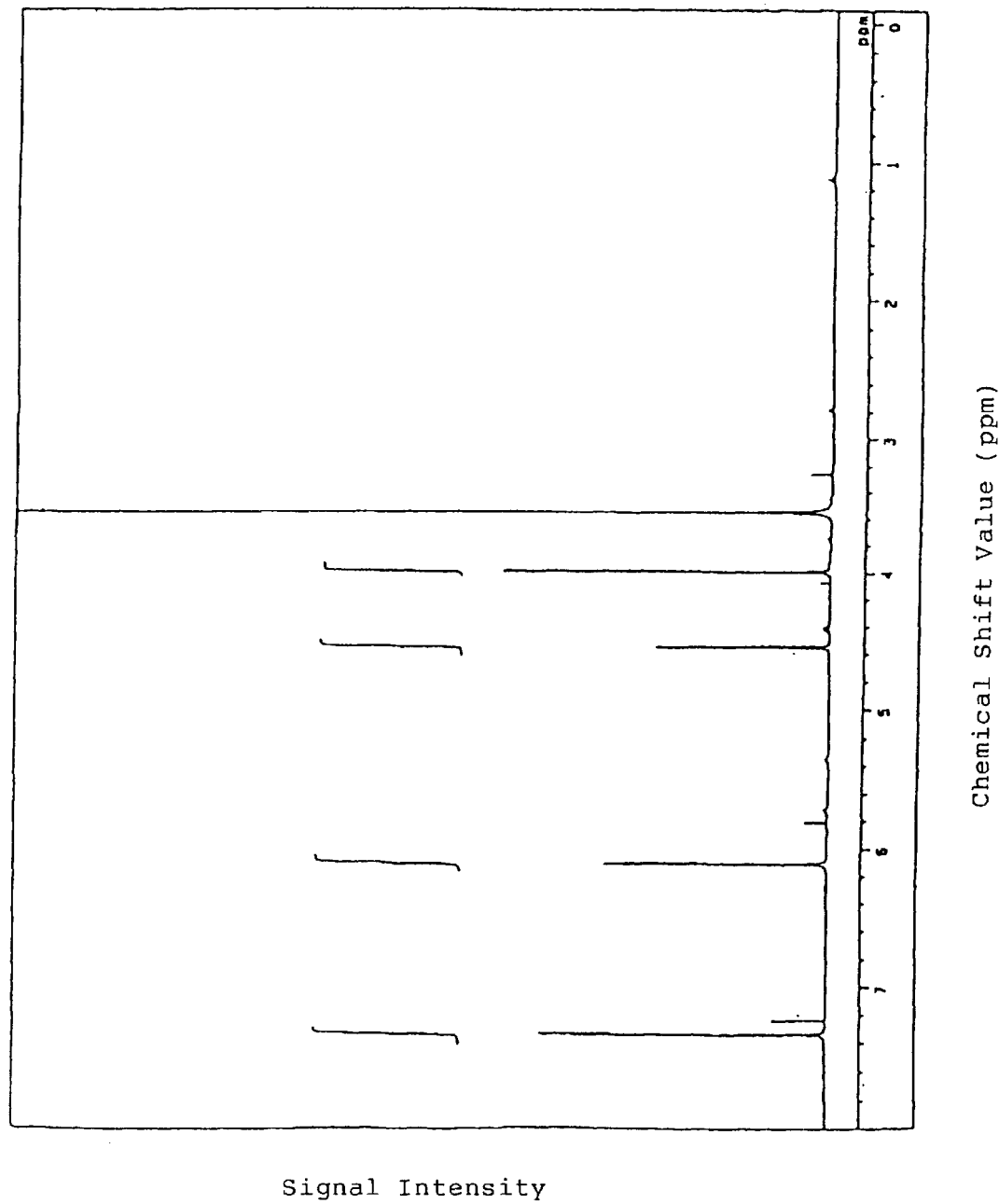
FIG. 11 shows a $^1$H—NMR spectrum of (−)-4,5-dihydroxy-2-cyclopenten-1-one.

FIG. 11 shows a $^1$H-NMR of the (−)-cyclopentenone where the ordinate shows signal intensity and the abscissa shows chemical shift values (ppm).

Figure 12:
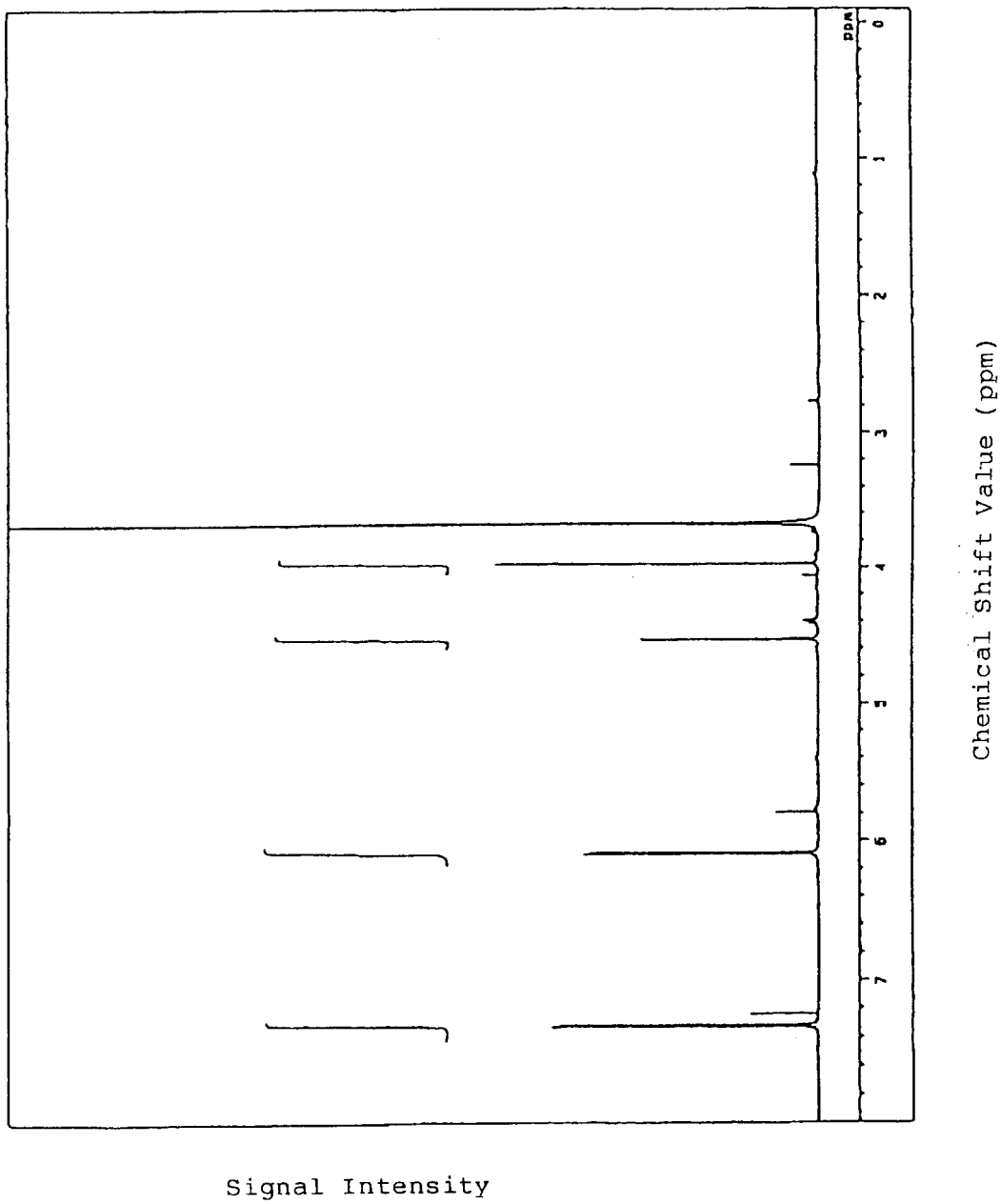
FIG. 12 shows a $^1$H—NMR spectrum of (+)-4,5-dihydroxy-2-cyclopenten-1-one.

FIG. 12 shows a $^1$H-NMR of the (+)-cyclopentenone where the ordinate shows signal intensity and the abscissa shows chemical shift values (ppm).

(2) Trans-cyclopentenone was synthesized by a method which was mentioned in the already-cited "Carbohydrate Research". Further, cis-cyclopentenone was synthesized by a method which was mentioned in the already-cited "Helvetica Chimica Acta". Each optically active substance thereof was prepared by means of an optical resolution.

Each of the prepared (+)-trans-cyclopentenone, (−)-trans-cyclopentenone, (+)-cis-cyclopentenone and (−)-cis-cyclopentenone was subjected to measurements of cell growth inhibition, apoptosis inducing activity, cancer cell differentiation inducing activity and antibacterial activity by the method for the corresponding examples whereupon each of (+)-trans-cyclopentenone, (−)-trans-cyclopentenone, (+)-cis-cyclopentenone and (−)-cis-cyclopentenone showed cell growth inhibiting activity, apoptosis inducing activity, cancer cell differentiation inducing activity and antibacterial activity.

Example 17

An ethanolic solution (1 mg/ml) of each of the (−)- and (+)-cyclopentenone obtained in Example 16 was diluted with a 75% aqueous ethanol solution to an extent of 2, 4, 8, 16, 32, 64, 128, 256, 512, 1024 and 2048-fold and each 5 μl of them was charged in each of the wells of a 96-well microtiter plate followed by drying with air. An RPMI 1640 medium (100 μl) containing 10% fetal bovine serum containing 5000 human promyelocytic leukemia cells HL-60 (ATCC CCL-240) was added to each well and incubated at 37° C. for 48 hours in the presence of 5% of carbon dioxide gas. After observing the morphology of the cells under an optical microscope, 10 μl of phosphate buffered saline containing 5 mg/ml of 3-(4,5-dimethylthiazol-2-yl)-2,5-diphenyltetrazolium bromide (MTT; manufactured by Sigma) thereto, an incubation was conducted for additional four hours and the growth state of the cells was observed under a microscope. Further, 100 μl of 2-propanol containing 0.04N HCl was added thereto followed by well stirring and an absorbance at 590 nm was measured and defined as the degree of cell growth.

The result was that, even in a fraction to which a 128-fold diluted solution of each of the optically active substances of the cyclopentenone was added (final concentration: 0.39 μg/ml), a cell growth inhibiting activity was noted. Further, an apoptosis inducing action was noted as well.

Example 18

(1) To an RPMI 1640 medium containing 10% of fetal bovine serum containing 1×10$^5$/ml of HL-60 cells was added 10, 1, 0.1 or 0.01 μg/ml of the cyclopentenone, then incubation was conducted at 37° C. in the presence of 5% of carbon dioxide gas for three or six days and the viable cell number were counted. The result on the sixth day of the incubation was that, as compared with the control to which no cyclopentenone was added, no viable cell was found in the fraction to which 10 μg/ml of the cyclopentenone was added while, in the fractions to which 1 μg/ml, 0.1 μg/ml and 0.01 μg/ml were added, cell growth inhibitions to an extent of about 90%, about 55% and about 40% were noted, respectively.

Figure 13:
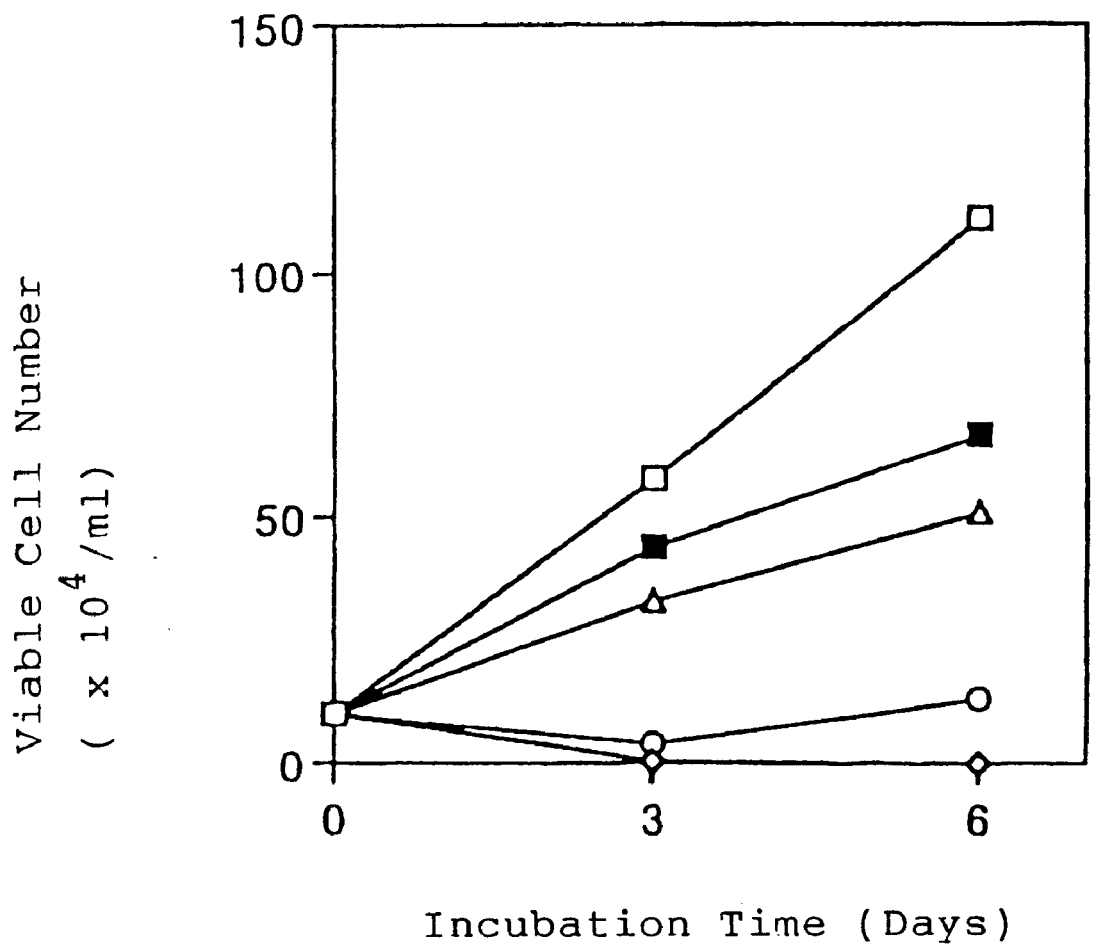
FIG. 13 shows the relation between the incubation time and the viable cell numbers in the medium.

The result is shown in FIG. 13. Thus FIG. 13 is to show a relation between the incubation time and the viable cell number in the cultured liquid when the cyclopentenone in various concentrations were added to the incubated liquid of HL-60 cells wherein the abscissa shows an incubation time (days) while the ordinate shows the viable cell number (x 10$^4$/ml) in the incubated liquid. In the curve, open square shows the case where no sample was added (control); open rhomb shows the case where 10 μg/ml of the cyclopentenone was added; open circle shows the case where 1 μg/ml was added; open triangle shows the case where 0.1 μg/ml was added; and black square shows the case where 0.01 μg/ml was added.

(2) To HL-60 cells was added 10$^{-4}$ μg/ml of the cyclopentenone and an incubation by the same manner as in Example 15-(1) was conducted for three days. A part of the cells was taken, smeared on a slide glass, subjected to a Wright-Giemsa stain which was mentioned in "Techniques of Tissue Culture" (edited by Japan Society of Tissue Culture; published by Asakura Shoten; 1982), page 191 and an observation was conducted under an optical microscope. The result was that the differentiated cells were around 10% in the control where no cyclopentenone was added while, in the fractions to which the cyclopentenone was added, 50% or more cells were differentiated to monocyte- or to macrophage-like cells.

Figure 14:
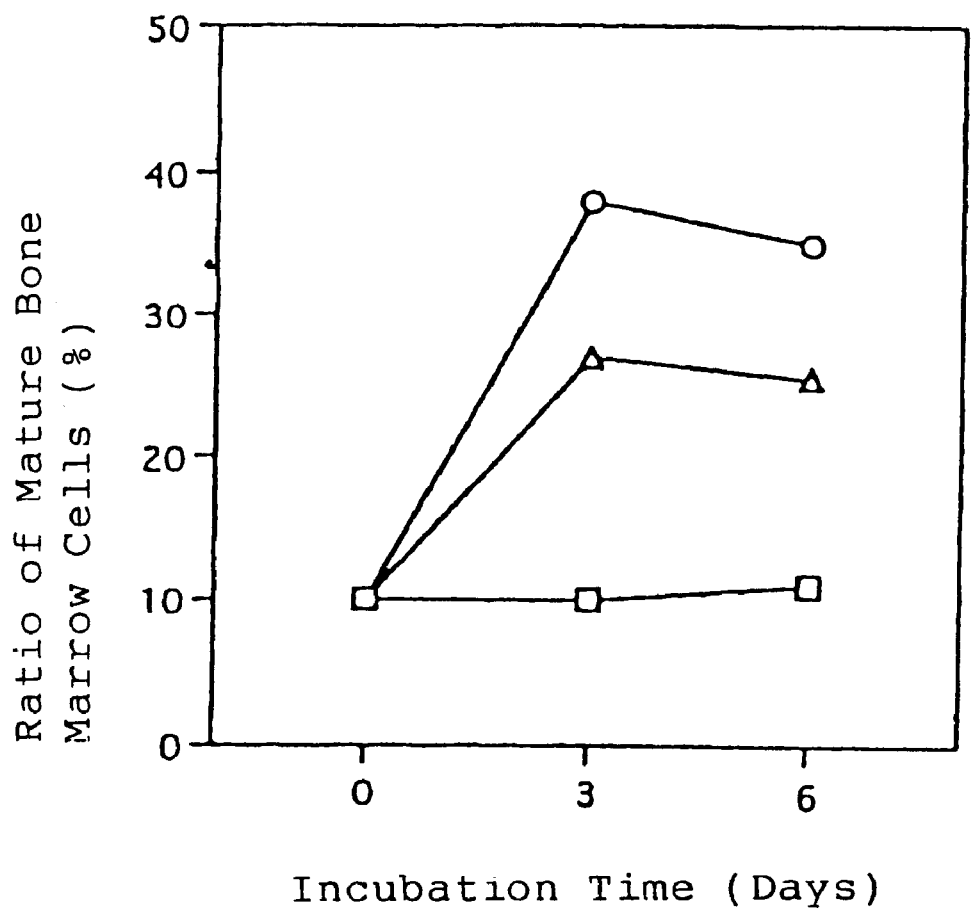
FIG. 14 shows the relation between the incubation time and the ratio occupied by the mature bone marrow cells in the incubated cells.

(3) To HL-60 cells was added 0.5 μg/ml or 0.005 μg/ml of the cyclopentenone and incubation was conducted by the same manner as in Example 18-(1) for three or six days. A part of the cells was taken, smeared on a slide glass, subjected to a Wright-Giemsa stain and an observation was conducted under an optical microscope. The result was that the differentiated cells were around 10% in the control where no cyclopentenone was added while, in the fraction to which 0.005 μg/ml of the cyclopentenone was added, 25% or more cells were differentiated to mature bone marrow cells. The results are shown in FIG. 14. Thus, FIG. 14 shows the relation between the incubation time and the ratio of mature bone marrow cells in the incubated cells where the abscissa shows incubation time (days) while the ordinate shows the ratio (%) of the mature bone marrow cells occupying in the incubated cells. In FIG. 14, open square shows the case where no sample was added (control); open circle shows the case where 0.5 μg g/ml of the cyclopentenone was added; and open triangle shows the case where 0.005 μg/ml of it was added.

Example 19

(1) Antibacterial action of the purified/isolated cyclopentenone mentioned in Example 3-(1) was measured using the following strains. Thus, the strains used for the measurement were as follows. Thus, tested microorganism (1): *Salmonella enteritidis* (a strain for a food poisoning case); tested microorganism (2): *Salmonella typhimurium* (a strain for a food poisoning case); tested microorganism (3): *Staphylococcus aureus* FRI 722 (a strain producing enterotoxin of type A); tested microorganism (4): *Staphylococcus aureus* (resisting to methicillin); tested microorganism (5): *Bacillus cereus* (a strain for a food poisoning of vomiting type); and tested microorganism (6): *Bacillus cereus* (a strain for a food poisoning of diarrhea type). All of those strains were stored at the Department of Hygienics, Kagawa Nutrition College.

Measurement of the antibacterial action was conducted using a growth inhibiting effect to each of the test microorganisms as an index. Thus, a certain amount of each of the test microorganisms was added to a medium containing the cyclopentenone of a certain concentration, the resulting test microorganism solution was incubated for 16 hours or 48 hours and the viable cell numbers thereafter were compared.

First, a certain concentration of the cyclopentenone was added to a sensitivity test broth (manufactured by Nissui) to conduct a continuous $2^n$ dilution. Then a microorganism solution subjected to a preincubation at 37° C. for 16 hours in a sensitivity test broth was inoculated in an amount of $10^6$ cells/ml and incubated at 37° C. Measurement of viable cell numbers for each incubation time for each strain was conducted after diluting the incubating solution to a certain extent followed by spreading on the surface of solid medium. In measurement of cell numbers for each microorganism, DHL (manufactured by Eiken), Baird Parker agar (manufactured by BBL) and NGKG agar (manufactured by Nissui) were used for Salmonella, *S. aureus* and *B. cereus*, respectively. With respect to *B. cereus* only, incubation was conducted at 32° C. The measured cell numbers at each incubation time were expressed in common logarithm as CFU (colony forming units)/ml. The following Table 10 shows the numbers of the tested microorganisms after incubation for 16 hours and Table 11 shows those after incubation for 48 hours. The cyclopentenone showed an antibacterial action to any of the tested organisms. Incidentally, in Tables 10–13, the sign (-) in the tables means that no growth of the test microorganism was noted.

TABLE 10

| Concentration of Added Sample in Incubating Solution of Tested Microorganism (ppm) | Numbers of Test Microorganism after Incubation for 16 Hours (CFU/ml) Test Microorganism | | | | | |
|---|---|---|---|---|---|---|
| | (1) | (2) | (3) | (4) | (5) | (6) |
| 1563 | — | — | — | — | — | — |
| 781 | — | — | — | — | — | — |
| 391 | — | — | 6.1 | — | — | — |
| 195 | 3.0 | 3.0> | 4.9 | 4.3 | — | — |
| 98 | 5.2 | 5.0 | 4.7 | 5.5 | 5.8 | 3.0 |
| 49 | 7.0 | 6.7 | 6.9 | 6.1 | 6.9 | 6.8 |
| 0 | 8.8 | 8.3 | 8.7 | 8.4 | 8.4 | 7.8 |

TABLE 11

| Concentration of Added Sample in Incubating Solution of Tested Microorganism (ppm) | Numbers of Test Microorganism after Incubation for 48 Hours (CFU/ml) Test Microorganism | | | | | |
|---|---|---|---|---|---|---|
| | (1) | (2) | (3) | (4) | (5) | (6) |
| 1563 | — | — | — | — | — | — |
| 781 | — | — | — | — | — | — |
| 391 | — | — | — | — | — | — |
| 195 | — | — | — | — | — | — |
| 98 | — | — | — | — | 8.1 | 5.0 |
| 49 | 9.0 | 8.5 | 8.5 | — | 8.4 | 7.9 |

(2) Antibacterial action of the above cyclopentenone to *Escherichia coli* and enterohemorrhagic *Escherichia coli* was measured. The tested microorganisms were as follows.

Tested microorganism (7): *Escherichia coli* (S-O157:H7, VT1,2-producing strain); tested microorganism (8): *Escherichia coli* (Y.3-O157:H7, VT1,2-producing strain); tested microorganism (9): *Escherichia coli* (Y.1-O157:H7, VT1-producing strain); tested microorganism (10): *Escherichia coli* (S-O26:HNM, VT1-producing strain); tested microorganism (11): *Escherichia coli* (S-O111:HNM, VT1,2-producing strain); and tested microorganism (12): *Escherichia coli* (isolated from food).

All of those strains were stored at the Department of Hygienics, Kagawa Nutrition College.

Measurement of the antibacterial action was conducted by the same manner as in Example 19-(1).

First, the cyclopentenone of a certain concentration was added to a sensitivity test broth (manufactured by Nissui) and a continuous $2^n$ dilution was conducted. Then a microorganism solution subjected to a preincubation at 37° C. for 16 hours in a sensitivity test broth was inoculated in an amount of $10^6$ cells/ml and incubated at 37° C. Measurement of viable cell numbers for each incubation time for each strain was conducted by means of a surface smear incubation after diluting the incubated solution to a certain extent. In measurement of cell numbers of the strain, DHL (manufactured by Eiken) was used. Measured cell numbers after each incubation time was expressed as a logarithmic value the same as above. The results are shown in the following Tables 12 and 13. The cyclopentenone showed an antibacterial action to any of the tested microorganisms.

TABLE 12

| Concentration of Added Sample in Incubating Solution of Tested Microorganism (ppm) | Numbers of Test Microorganism after Incubation for 16 Hours (CFU/ml) Test Microorganism | | | | | |
|---|---|---|---|---|---|---|
| | (7) | (8) | (9) | (10) | (11) | (12) |
| 1563 | — | — | — | — | — | 3.0> |
| 781 | — | — | 3.0> | — | — | 6.4 |
| 391 | 3.6 | 2.2 | 3.0> | — | 3.6 | 5.8 |
| 195 | 4.7 | 4.7 | 3.0> | — | 6.2 | 6.6 |
| 98 | 7.0 | 7.0 | 7.1 | 6.1 | 7.4 | 8.3 |
| 49 | 6.3 | 6.9 | 7.1 | 7.1 | 8.0 | 8.2 |
| 0 | 8.5 | 8.0 | 8.6 | 8.5 | 8.5 | 8.5 |

TABLE 13

| Concentration of Added Sample in Incubating Solution of Tested Microorganism (ppm) | Numbers of Test Microorganism after Incubation for 48 Hours (CFU/ml) Test Microorganism | | | | | |
|---|---|---|---|---|---|---|
| | (7) | (8) | (9) | (10) | (11) | (12) |
| 1563 | — | — | — | — | — | — |
| 781 | — | — | — | — | — | — |
| 391 | — | — | — | — | — | — |
| 195 | — | — | — | — | 4.1 | — |
| 98 | 8.9 | 5.3 | 8.6 | 7.4 | 8.5 | 5.0 |
| 49 | 8.5 | 9.3 | 8.5 | 9.8 | 8.5 | 10.1 |

(3) The followings were used as testing microorganism for measuring the antibacterial activity of the above cyclopentenone. They were testing microorganism (13): *Escherichia coli* HB101 (ATCC 33694); testing microorganism (14): *Salmonella typhimurium* LT-2 (ATCC 27106); testing microorganism (15): *Pseudomonas aeruginosa* (IFO 3080); testing microorganism (16): *Staphylococcus aureus* 3A (NCTC 8319); testing microorganism (17): *Bacillus subtilis* (IFO 3034); and testing microorganism (18): *Streptococcus mutans* (GS5; stored at National Institute of Health).

The testing microorganisms were subjected to a seed culture overnight in an L-broth (1% tryptone, 0.5% yeast extract and 5% NaCl; pH 7.0). The seed culture (5 μl) was inoculated to a medium to which 25–200 μg/ml of cyclopentenone was added to 5 ml of L-both and also to a medium to which nothing was added and a shake incubation was conducted at 37° C. to measure the growth. At the initiation of the incubation and also at eight hours thereafter, turbidity of the culture was measured using a Fuji Digital Turbidimeter (sold from Fuji Kogyo KK; manufactured by Akiyama Denki Seisakusho) under the condition that the adjusted scale was 82.3 and the growth of the tested microorganism was measured from the value (growth turbidity) obtained by deducting the turbidity at the initiation of incubation from that after eight hours. Incidentally, in the case of the testing microorganism (18), a brain heart infusion was used instead of L-broth.

The results are shown in Table 14 where "-" means uninvestigated.

TABLE 14

| Tested Microorganism | (Growth Turbidity) Amount of the Cyclopentenone Added ($\mu$g/ml medium) | | | | |
|---|---|---|---|---|---|
| | 0 | 25 | 50 | 100 | 200 |
| (13) | 222 | 0 | 0 | 0 | 0 |
| (14) | 273 | — | — | 0 | 0 |
| (15) | 239 | 2 | 0 | 0 | 0 |
| (16) | 243 | 203 | 158 | 0 | 0 |
| (17) | 267 | 145 | 9 | 0 | 0 |
| (18) | 140 | 133 | 130 | 34 | 6 |

Thus, the cyclopentenone showed an antibacterial activity to all of the microorganisms tested.

(4) Antibacterial activity of the cyclopentenone to hiochi bacteria was tested by the following methods. The testing microorganism was subjected to a stationary incubation for five days in an SI medium (Japan Brewery Association) containing 10% of ethanol to give a seed microorganism. The seed microorganism (0.1%) was added to 100 ml of 10% ethanol-containing SI medium to which the cyclopentenone was added in an amount of 0, 25, 50, 75 or 100 $\mu$g/ml (in terms of final concentration), then a stationary incubation was conducted for five days and the turbidity was measured. In measuring the turbidity, the value of $OD_{600}$ was measured using an absorbance meter. A value of $OD_{600}$ of the medium to which no testing microorganism was inoculated was deducted from the above value and this (growth turbidity) was used for the growth of the tested microorganism.

The tested microorganisms were as follows. Thus, *Lactobacillus fructivorans* (IFO 13118) (testing microorganism A), *Lactobacillus fructivorans* (JCM 1198) (testing microorganism B) and *Lactobacillus homohiochii* (IFO 13120) (testing microorganism C) as true hiochi bacteria while *Lactobacillus rhamnosus* (IFO 3532) (testing microorganism D) was used as hiochi lactobacteria. The results are shown in Table 15.

TABLE 15

| Tested Microorganism | (Growth Turbidity) Amount of the Cyclopentenone Added ($\mu$g/ml medium) | | | |
|---|---|---|---|---|
| | 0 | 25 | 50 | 75 |
| A | 0.96 | 0.17 | 0.02 | 0 |
| B | 2.03 | 0.01 | 0 | 0 |
| C | 1.61 | 0.32 | 0.08 | 0 |
| D | 0.35 | 0.04 | 0.01 | 0 |

Growth of the tested microorganisms A, C and D was completely inhibited by 75 $\mu$g/ml while that of the tested microorganism B was completely inhibited by 50 $\mu$g/ml. Thus, the cyclopentenone showed an antibacterial action to hiochi bacteria as well.

Further, the cyclopentenone showed an antimicrobial activity at high concentrations to fungi such as *Saccharomyces cerevisiae* ATCC 9763, *Candida albicans* TIMM 0136 and *Aspergillus fumigatus* TIMM 1776 as well.

Example 20

(1) *Vibrio parahaemolyticus* 4387-61 or *Vibrio parahaemolyticus* T4144-1 (both stored at National Institute of Hygienic Sciences) was inoculated to make $10^6$ cells/ml to a trypto-soya bouillon medium (manufactured by Nissui) containing 800, 400, 200, 100, 5, 25, 12.5, 6.15, 3.13 or 1.56 $\mu$g/ml of the cyclopentenone and a stationary incubation was conducted at 37° C. for 24 hours. The result was that, in any of the strains, no growth of the microorganism was noted in the fractions where 12.5 $\mu$g/ml or more cyclopentenone was added.

The culture (50 $\mu$l) where no growth of the microorganism was noted was spread on 20 ml of a trypto-soya bouillon agar medium containing no cyclopentenone and incubation was conducted at 37° C. for 24 hours. The result was that, in any of the strains, no growth of microorganism was noted on the agar medium on which a fraction (to which 50 $\mu$g/ml or more cyclopentenone was added) was spread.

From the above, the cyclopentenone showed an antibacterial action to *Vibrio parahaemolyticus* 4387-61 and to *Vibrio parahaemolyticus* T4144-1 at 12.5 $\mu$g/ml and showed a bactericidal action to both strains at 50 $\mu$g/ml.

(2) *Campylobacter jejuni* A3309 (stored at the Institute of Hygienic Sciences) was inoculated to a brain heart infusion medium (manufactured by Difco) containing 2% of calf serum (manufactured by Dainippon Seiyaku) and subjected to a shake preincubation at 37° C. for 16 hours. The culture (50 $\mu$l) was spread on 20 ml of 0.5% NaCl-containing Muller-Hinton plate medium (manufactured by BBL) containing 800, 400, 200, 100, 50, 25, 12.5, 6.25, 3.13 or 1.56 $\mu$g/ml of cyclopentenone and subjected to a stationary incubation at 37° C. for 48 hours.

The result was that no growth of the microorganism was noted on the plate medium to which 12.5 $\mu$g/ml or more cyclopentenone was added.

Thus, the cyclopentenone showed an antibacterial action to Campylobacter.

(3) Measurement of antibacterial action of the cyclopentenone to *Legionella pneumophila* (isolated from a washing of human bronchus; testing microorganism (1)) and *Legionella pneumophila* (isolated from bathtub water of hot spring; testing microorganism (2)) (both stored at Department of Hygienics, Kagawa Nutrition College) was conducted using the growth-inhibiting effect to each of the testing microorganisms as an index. Thus, a certain amount of each of the testing microorganisms was added to a liquid medium containing a certain concentration of the cyclopentenone, the resulting testing microorganism suspension was incubated for 16 hours, 48 hours, 72 hours or 96 hours and the viable cell numbers after incubation were checked.

First, a certain concentration of cyclopentenone was added to a BCYE α broth (manufactured by Oxoid) and subjected to a $2^n$ continuous dilution. A bacterial suspension preincubated at 37° C. for 16 hours in a BCYE α broth was added thereto to make the cell numbers $10^6$/ml and incubated at 37° C. Measurement of the viable cell numbers for each incubation time for each microorganism was conducted by an appropriate dilution of the culture followed by spreading on the BCYE α agar (manufactured by Oxoid).

The measured cell numbers for each incubation time was given a CFU (colony forming units)/ml in terms of comon logarithm. The results are shown in the following Table 16. The cyclopentenone showed an antibacterial action to any of the microorganisms. Incidentally, "-" in the table means that no growth of the tested microorganism was noted.

TABLE 16

| Concentration of the Added Sample in the Culture of the Tested Microorganism (ppm) | Numbers of Tested Microorganism Cells after each Incubation (CFU/ml) | | | |
|---|---|---|---|---|
| | (16-hr incubation) | | (96-hr incubation) | |
| | Tested Microorganism | | | |
| | (1) | (2) | (1) | (2) |
| 24 | — | — | — | — |
| 12 | 5.7 | 6.1 | 8.3 | 8.6 |
| 0 | 6.9 | 7.4 | 8.7 | 8.6 |

(4) As to *Helicobacter pylori* strains, a standard strain NCTC 11637 (ATCC 43504) and clinically isolated strains from human stomach (206 and 3401; both stored at Department of Bacteriology, Hyogo Medical College) were used. Each strain was subjected to a shake incubation at 37° C. under a slightly aerophilic condition using an Aneropack Campiro (manufactured by Mitsubishi Gas Chemical) in a Brucella Broth Medium (manufactured by BBL) containing 7% of horse serum (manufactured by Bio Whittaker). The microorganism in a logarithmic growth phase was diluted with a Brucella Broth and used for the test. A 24-well plate (manufactured by Falcon) was used for the experiments. The cyclopentenone was charged at the rate of 0.1 ml (1,000 μg)/well, subjected to a two-step dilution using PBS and immobilized by adding 0.9 ml/well of a medium [a Brucella agar medium (pH 6.0) containing 7% of horse serum (manufactured by BBL)]. The Brucella agar medium was previously adjusted to pH 6.0 with HCl and was used for the experiments. Each microorganism was inoculated at the rate of about $10^4/50$ μl/well. After inoculation of the microorganism, incubation was conducted under a slightly aerophilic condition at 37° C. for 3–4 days to judge the antibacterial activity. The amount of a sample (μg/ml) showing 90% or more inhibition was defined as the MIC. The result was that, to all of the stains tested, the MIC was 32 μg/ml and the cyclopentenone showed an antibacterial action to Helicobacter strains.

Example 21

Anticancer Action of the Cyclopentenone to Solid Cancer

The cyclopentenone mentioned in Example 3-(1) was diluted with a physiological saline solution to certain concentrations and the following tests were conducted.

(1) Meth A cells ($2\times10^6$ cells/mouse) was subcutaneously injected to abdomen of female BALB/c mice of eight weeks age (body weight: about 20 g). After that, the cyclopentenone (5 mg/kg/day) was subcutaneously injected to the same area for continued five days. On the other hand, a physiological saline solution was subcutaneously injected to a control group by the same manner. After two weeks, cancer tissues generated in abdomen of the mice was excised and the weight was measured. The result is given in Table 17.

Thus, in the control group, average weight of the cancer was 1.41 g while, in the group administered with the cyclopentenone (5 mg/kg/day), the weight was 0.0 g whereby generation of cancer tissue was not noted at all and the inhibiting rate was 100%.

TABLE 17

| Mice (%) | (n) | Tumor Weight (g) (average ± SD) | Inhibiting Rate |
|---|---|---|---|
| Control | (7) | 1.41 ± 0.55 | — |
| Administered with Cyclopentenone | (8) | 0.00 ± 0.00 | 100.0 |

(2) Sixteen female mice of ICR strain of six weeks age (body weight: about 26 g) were used. Sarcoma-180 ($5.5\times10^6$ cells/mouse) was subcutaneously injected into abdomen whereupon a control group (8 mice) and a group administered with the cyclopentenone (8 mice) were made.

The cyclopentenone was diluted with tap water and freely given to the cyclopentenone-administered group to make the dose of the cyclopentenone about 80 mg/kg/day using a water-supplying bottle. Tap water was similarly given to the control group. In both groups, feed was freely given during the course of the experiment.

Numbers of living mice on the 40th day after subcutaneous transplantation of Sarcoma-180 were two out of eight in the control group while those in the cyclopentenone-administered group were seven whereupon a significant life-prolonging effect by administration of the cyclopentenone was noted.

Figure 15:
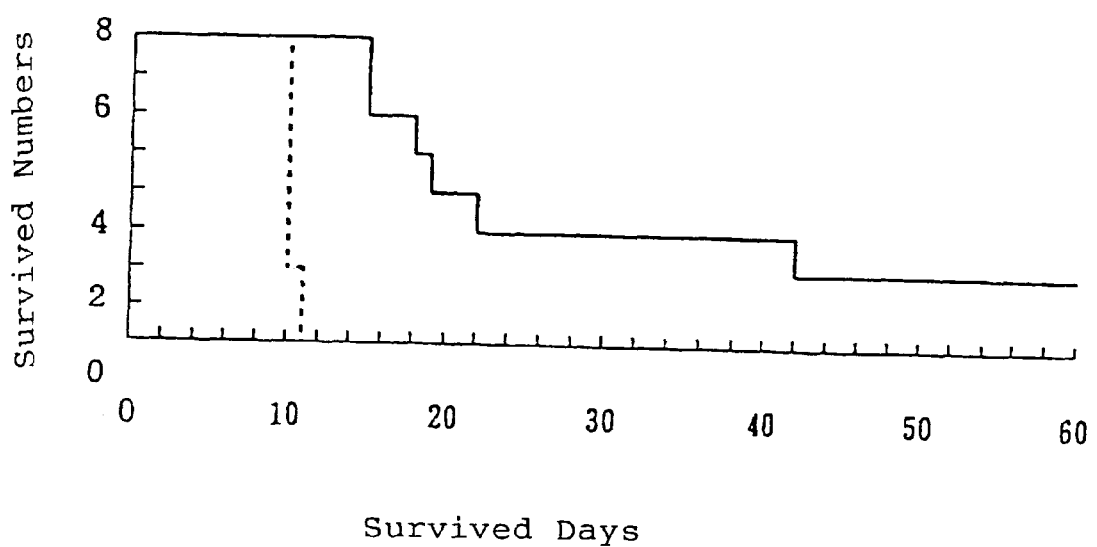
FIG. 15 shows the anticancer action of the cyclopentenone.

(3) Mouse leukemia P-388 ($1.1\times10^6$ cells/mouse) was intraperitoneally injected to female DBA/2 mice of seven weeks age (body weight: about 20 g). After that, the cyclopentenone (10 mg/kg/day) was intraperitoneally injected for continued five days. In the meanwhile, a physiological saline solution was intraperitoneally injected to a control group by the same manner. In two groups (each comprising eight mice), survived numbers of mice, average surviving days and life-prolonging rate were calculated. The results are shown in FIG. 15. Thus, in the control group, average surviving days were 10.3 days while, in the cyclopentenone-administered group, they were 31.4 days and the life-prolonging rate was 306.1% showing a significant life-prolonging effect. FIG. 15 shows the anticancer effect of the cyclopentenone where the ordinate shows survived numbers of mice while the abscissa shows survived days. In FIG. 15, a solid line shows the cyclopentenone-administered group while a broken line shows the control group.

Similarly, 16 female mice of an ICR strain of five weeks age (body weight: about 25 g) were used and Sarcoma-180 ($5.5\times10^6$ cells/mouse) was intraperitoneally injected to set up a control group (comprising eight mice) and a cyclopentenone-administered group (comprising eight mice).

In the meanwhile, 16 female mice of a CDF1 strain of seven weeks age (body weight: about 20 g) were used and IMC ($2.0\times10^6$ cells/mouse) was intraperitoneally injected to set up a control group (comprising eight mice) and a cyclopentenone-administered group (comprising eight mice).

Further, 16 female mice of a DDY strain of five weeks age (body weight: about 25 g) were used and EAC ($1.2\times10^6$ cells/mouse) was intraperitoneally injected to set up a control group (comprising eight mice) and a cyclopentenone-administered group (comprising eight mice).

The results were that, in the cases of Sarcoma-180, IMC and EAC, the mean survival days of the control groups were 22.6 days, 10.8 days and 15.8 days, respectively while those of the cyclopentenone-administered group were 33.4 days, 20.3 days and 40.3 days, respectively wherein the increase in life span were 148%, 188% and 255%, respectively showing a significant life-prolonging effect by administration of the cyclopentenone.

Example 22

Injections (1) The cyclopentenone was added in a concentration of 1% to a physiological saline solution (Japanese Pharmacopoeia) to prepare an injection solution.

(2) To a physiological saline solution (the same as above) were added the cyclopentenone and glycyrrhetinic acid in concentrations of 0.5% and 0.1%, respectively to prepare an injection solution.

Example 23

Tablets (1) Tablets where each contains 100 mg of the cyclopentenone and a certain amount of microcrystalline cellulose were prepared followed by sugar-coating to prepare tablets.

(2) Tablets where each contains 0.1 mg of the cyclopentenone, 10 mg of dipotassium glycyrrhetinic acid and a certain amount of microcrystalline cellulose were prepared followed by sugar-coating to prepare tablets.

Example 24

Ointments

An ointment was prepared according to the following formulation.

| | |
|---|---|
| The cyclopentenone | 1 g |
| Absorption ointment (Japanese Pharmacopoeia) | 99 g |

First, the cyclopentenone was well kneaded with a small amount of absorption ointment and then the remaining absorption ointment was gradually added thereto followed by kneading until a homogeneous product was resulted to prepare an ointment.

This ointment is applied 4–5 times a day to the lesion.

Example 25

Cosmetics

A lotion in a form of an antibacterial cosmetic material was prepared according to the following formulation.

| | |
|---|---|
| Ethanol | 10 parts |
| Glycerol | 1 part |
| Citric acid | 0.3 part |
| Methyl p-hydroxybenzoate | 0.2 part |
| The cyclopentenone | 0.1 part |
| Perfume | a little |
| Pure water added to make | 100 parts |

Example 26

Bathing Agent

Antibacterial bathing agent was prepared according to the following formulation.

| | |
|---|---|
| Anhydrous Glauber's salt | 20 parts |
| Sodium bicarbonate | 40 parts |
| Succinic acid | 10 parts |
| The cyclopentenone | 30 parts |
| Dyes | q.s. |
| Perfumes (prepared in a form of tablets) | q.s. |

Example 27

Dentifrice

Dentifrice was prepared according to the following formulation.

| | |
|---|---|
| Calcium carbonate | 50.00% |
| Glycerol | 20.00% |
| Carrageenan | 0.50% |
| Carboxymethylcellulose | 1.00% |
| Lauryl diethanolamide | 1.00% |
| Sucrose monolaurate | 2.00% |
| Perfumes | 1.00% |
| Saccharine | 0.10% |
| The cyclopentenone | 0.10% |
| Water | balance |
| Total | 100.00% |

Example 28

Tablet candy was prepared according to the following formulation.

| | |
|---|---|
| Sugar | 74.9% |
| Lactose | 20.0% |
| Sucrose monolaurate | 0.2% |
| Perfumes | 0.5% |
| Pure water | 4.3% |
| The cyclopentenone | 0.001% |

Example 29

Antibacterial beverages were prepared according to the following methods.

(1) Pectin (Pomosin Pectin LM-13CG; manufactured by Hercules) (5 kg) was added to 100 liters of tap water and the mixture was heated from the liquid temperature of 28° C. to 120° C. by means of blowing steam thereinto during 35 minutes, kept at 120° C. for five hours with stirring and cooled to prepare 135 liters of cooled mixture. To this were added 1.35 kg of Celite #545 (manufactured by Celite) and 1.35 kg of Silica #600-S (manufactured by Chuo Silica) as filter aids and filtration was conducted using a compact filter (6-inch filter paper in 16 stages; ADVANTEC #327) precoated with 0.1 kg of Celite #545 and 0.1 kg of Silica #600-S. The resulting filtrate was subjected to a continuous instant heating treatment (at 98° C. for 60 seconds) using a plate heater (manufactured by Nichihan Seisakusho) followed by cooling to prepare 150 liters of heat-treated pectin solution containing the cyclopentenone.

Said heat-treated pectin solution containing the cyclopentenone had pH of about 3.5, acidity of 6.2 ml and sugar degree of 5.8 Brix %. Incidentally, pH was measured by a pH meter, acidity was expressed in terms of the amount (ml) of 0.1N NaOH used for neutralizing to pH 7.0 and sugar degree was measured by a Brix saccharometer.

(2) Green tea was prepared by a conventional means using 10 g of green tea leaf, 0.2 g of vitamin C and 1,000 ml of deionized water. The already-prepared heat-treated pectin solution containing the cyclopentenone was added in an amount of 200 mg (on a solid base; containing 1.6 mg of the cyclopentenone) to 100 ml of the green tea to prepare a product (1) of the invention. The control was that to which nothing was added. An organoleptic evaluation (by a five-point method where point 5 was good and point 1 was bad) was conducted by 20 panelists and the averages of the results are shown in Table 18.

TABLE 18

| | Organoleptic Evaluation | |
|---|---|---|
| | Product (1) | Control |
| Breadth of Taste | 4.3 | 3.2 |
| Balance of Taste | 3.9 | 3.4 |
| Total Taste | 4.3 | 3.3 |

From Table 18, the evaluation was that, as compared with the control, the product (1) of the present invention had wider and broader taste and well-balance taste whereupon flavor and taste of the tea were improved and an effect of "a hidden flavor" was achieved.

Example 30

Beverage was prepared according to the following formulation.

| | |
|---|---|
| Fructose-Glucose-Liquid Sugar | 5.00% |
| Sugar | 4.00% |
| Acidic agent | 1.20% |
| Perfumes | 0.30% |
| Cyclopentenone-containing material | 0.5% |
| Pure water | balance |
| Total | 100.00% |

The heat-treated pectin solution containing the cyclopentenone mentioned in Example 29-(1) was used as the cyclopentenone-containing material and its amount calculated on a solid basis was added. This beverage (100 ml) contains 4 mg of the cyclopentenone.

Example 31

Fresh cabbage (200 g) was cut into strips and each 100 g was dipped in water (control) or in a 0.2% solution of the cyclopentenone for five minutes. Then water as gently removed therefrom and the cabbage was placed in a bag made of synthetic resin and allowed to stand at room temperature (20° C.). In the observation after 24 hours, the cabbage dipped in the aqueous solution of the cyclopentenone kept freshness as compared with that dipped in water (control).

Such a difference became clearer with a lapse of days and, in the observation after four days, the cabbage dipped in the aqueous solution of the cyclopentenone showed no bad smell keeping the freshness as compared with that dipped in water (control).

MERIT OF THE INVENTION

The present invention offers the cyclopentenone and optically active substances thereof which exhibit physiological activities such as anticancer action, inhibiting action to cancer cell proliferation, inducing action for cancer cell differentiation, apoptosis inducing action, antibacterial action, etc. and have a high safety. It also offers pharmaceuticals, food and beverages having such physiological activity functions containing said compounds. It is now possible in accordance with the present invention to manufacture the cyclopentenone easily and efficiently from natural materials and to offer the optically active substances thereof in low cost.

Due to their physiological activities, the cyclopentenone and/or its optically active substances offered by the present invention can be used as pharmaceuticals having preventive effect of carcinogenicity, anticancer effect and antibacterial action and said pharmaceuticals are useful for keeping the homeostatis of living body, particularly for keeping the good health of stomach and intestine. The present invention also offers antiseptics, antibacterial cosmetics, antibacterial dentifrices and antibacterial bathing agents containing the cyclopentenone and/or its optically active substances as effective ingredients.

In accordance with the present invention, it is now possible that an appropriate amount of the cyclopentenone and/or its optically active substances having a physiological activity is contained in food or beverages. Because of various physiological activities of the cyclopentenone and its optically active substances, food or beverage of the present invention is a health food or beverage having a function of keeping homeostatis of living body such as prevention of carcinogenicity, anticancer effect, antibacterial effect and apoptosis inducing action and the present invention offers food or beverage containing a functional substance useful for keeping the good health of stomach and intestine. Moreover, as a result of addition of the cyclopentenone, the antibacterial action of food or beverage can be easily potentiated and the preparation containing the cyclopentenone and/or its optically active substances is quite useful as an antiseptic agent for food or beverage as well.

In addition, the present invention offers a substance which contains a saccharide compound containing uronic acid and/or uronic acid derivative(s) where, in said substance which contains a saccharide compound containing uronic acid and/or uronic acid derivative(s), at least a part of reactivity of amines, amino acids, peptides or protein having a reactivity with uronic acid, uronic acid derivative(s), an intermediate for the cyclopentenone or the cyclopentenone disappears and/or at least a part of said reactive substance(s) is removed. When said substance which contains a saccharide compound containing said uronic acid and/or uronic acid derivative(s) is used, the cyclopentenone and/or its optically active substances used in the present invention can be efficiently manufactured. Examples of the substance which contains the saccharide compound containing said uronic acid and/or uronic acid derivative(s) are dry-heated substance which contains a saccharide compound containing uronic acid and/or uronic acid derivative(s). With regard to the dry heating treatment, a roasting/parching treatment is simple and convenient and roasted/parched plants, animals and microorganisms such as roasted/parched vegetables, fruits, cereals, mushrooms, sea algae, cortex and cartilage are quite useful in the manufacture of the cyclopentenone and/or its optically active substances of the present invention. Incidentally, the dry-heat treated product can be efficiently prepared by dehydrating the substance to be treated before the dry-heating treatment.

What is claimed is:

1. A method of manufacturing 4,5-dihydroxy-2-cyclopenten-1-one represented by the following formula [1]

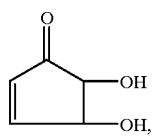

which comprises heating at least one substance selected from the following (a), (b) and (c) to produce the 4,5-dihydroxy-2-cyclopenten-1-one,
- (a): uronic acid or at least one uronic acid derivative selected from the group consisting of uronic acid salt, uronic acid lactone, a salt of uronic acid lactone, uronic acid ester, a salt of uronic acid ester, uronic acid amide and a salt of uronic acid amide;
- (b): a saccharide compound which contains uronic acid and/or said at least one uronic acid derivative; and
- (c): a substance containing a saccharide compound which contains uronic acid and/or said at least one uronic acid derivative.

2. A method of manufacturing 4,5-dihydroxy-2-cyclopenten-1-one represented by the following formula [1]

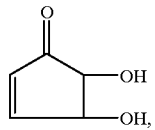

which comprises heating at least one substance selected from the following (a), (b) and (c) to produce the 4,5-dihydroxy-2-cyclopenten-1-one,
- (a): uronic acid or at least one uronic acid derivative selected from the group consisting of uronic acid salt, uronic acid lactone, a salt of uronic acid lactone, uronic acid ester, a salt of uronic acid ester, uronic acid amide and a salt of uronic acid amide;
- (b): a saccharide compound which contains uronic acid and/or said at least one uronic acid derivative; and
- (c): a substance containing a saccharide compound which contains uronic acid and/or said at least one uronic acid derivative, and recovering the 4,5-dihydroxy-2-cyclopenten-1-one from the heat-treated product.

3. A method of manufacturing an optically active compound of 4,5-dihydroxy-2-cyclopenten-1-one which comprises
- (A): heating at least one substance selected from the following (a), (b) and (c) to produce the 4,5-dihydroxy-2-cyclopenten-1-one,
- (a): uronic acid or at least one uronic acid derivative selected from the group consisting of uronic acid salt, uronic acid lactone, a salt of uronic acid lactone, uronic acid ester, a salt of uronic acid ester, uronic acid amide and a salt of uronic acid amide;
- (b): a saccharide compound which contains uronic acid and/or said at least one uronic acid derivative; and
- (c): a substance containing a saccharide compound which contains uronic acid and/or said at least one uronic acid derivative;
- (B): optionally, isolating the 4,5-dihydroxy-2-cyclopenten-1-one from the resulting heat-treated product; and
- (C): subjecting the 4,5-dihydroxy-2-cyclopenten-1-one to an optical resolution.

4. An anticancer agent which is characterized in containing 4,5-dihydroxy-2-cyclopenten-1-one represented by the formula [1] and/or an optically active compound thereof,

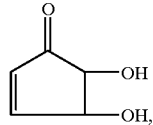

wherein the anticancer agent contains 4,5-dihydroxy-2-cyclopenten-1-one represented by the formula [1] obtained by the method according to claim 1 as effective ingredient(s).

5. An anticancer agent which is characterized in containing 4,5-dihydroxy-2-cyclopenten-1-one represented by the formula [1] and/or an optically active compound thereof,

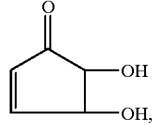

wherein the anticancer agent contains the heat-treated product according to claim 1 as effective ingredient(s).

6. An anticancer agent which is characterized in containing 4,5-dihydroxy-2-cyclopenten-1-one represented by the formula [1] and/or an optically active compound thereof,

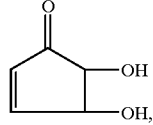

wherein the anticancer agent contains 4,5-dihydroxy-2-cyclopenten-1-one represented by the formula [1] obtained by the method according to claim 2 as effective ingredient(s).

7. A cancer cell differentiation inducer which is characterized in containing 4,5-dihydroxy-2-cyclopenten-1-one represented by the formula [1] and/or an optically active compound thereof,

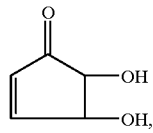

wherein the cancer cell differentiation inducer contains 4,5-dihydroxy-2-cyclopenten-1-one represented by the formula [1] obtained by the method according to claim 1 as effective ingredient(s).

8. A cancer cell differentiation inducer which is characterized in containing 4,5-dihydroxy-2-cyclopenten-1-one represented by the formula [1] and/or an optically active compound thereof,

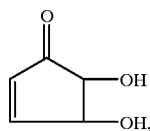

wherein the cancer cell differentiation inducer contains the heat-treated product according to claim 1 as effective ingredient(s).

9. A cancer cell differentiation inducer which is characterized in containing 4,5-dihydroxy-2-cyclopenten-1-one represented by the formula [1] and/or an optically active compound thereof,

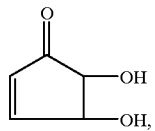

wherein the cancer cell differentiation inducer contains 4,5-dihydroxy-2-cyclopenten-1-one represented by the formula [1] obtained by the method according to claim 2 as effective ingredient(s).

10. An apoptosis inducer which is characterized in containing 4,5-dihydroxy-2-cyclopenten-1-one represented by the formula [1] and/or an optically active compound thereof,

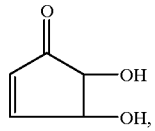

wherein the apoptosis inducer contains 4,5-dihydroxy-2-cyclopenten-1-one represented by the formula [1] obtained by the method according to claim 1 as effective ingredient (s).

11. An apoptosis inducer which is characterized in containing 4,5-dihydroxy-2-cyclopenten-1-one represented by the formula [1] and/or an optically active compound thereof,

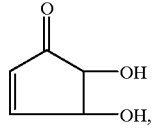

wherein the apoptosis inducer contains the heat-treated product according to claim 1 as effective ingredient(s).

12. An apoptosis inducer which is characterized in containing 4,5-dihydroxy-2-cyclopenten-1-one represented by the formula [1] and/or an optically active compound thereof,

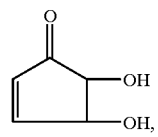

wherein the apoptosis inducer contains 4,5-dihydroxy-2-cyclopenten-1-one represented by the formula [1] obtained by the method according to claim 1 as effective ingredient (s).

13. An antibacterial agent which is characterized in containing 4,5-dihydroxy-2-cyclopenten-1-one represented by the formula [1] and/or an optically active compound thereof,

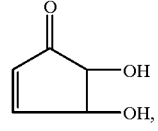

wherein the antibacterial agent contains 4,5-dihydroxy-2-cyclopenten-1-one represented by the formula [1] obtained by the method according to claim 1 as effective ingredient (s).

14. An antibacterial agent which is characterized in containing 4,5-dihydroxy-2-cyclopenten-1-one represented by the formula [1] and/or an optically active compound thereof,

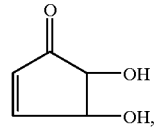

wherein the antibacterial agent contains the heat-treated product according to claim 1 as effective ingredient(s).

15. An antibacterial agent which is characterized in containing 4,5-dihydroxy-2-cyclopenten-1-one represented by the formula [1] and/or an optically active compound thereof,

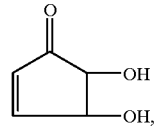

wherein the antibacterial agent contains 4,5-dihydroxy-2-cyclopenten-1-one represented by the formula [1] obtained by the method according to claim 2 as effective ingredient (s).

16. A method for the induction of cancer cell differentiation which is characterized in using 4,5-dihydroxy-2-cyclopenten-1-one represented by the formula [1] and/or an optically active compound thereof as effective ingredient(s),

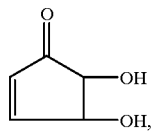

wherein the method uses 4,5-dihydroxy-2-cyclopenten-1-one represented by the formula [1] obtained by the method according to claim 1 as effective ingredient(s).

17. A method for the induction of cancer cell differentiation which is characterized in using 4,5-dihydroxy-2-cyclopenten-1-one represented by the formula [1] and/or an optically active compound thereof as effective ingredient(s),

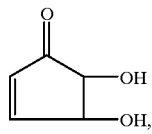

wherein the method uses the heat-treated product according to claim 1 as effective ingredient(s).

18. A method for the induction of cancer cell differentiation which is characterized in using 4,5-dihydroxy-2-cyclopenten-1-one represented by the formula [1] and/or an optically active compound thereof as effective ingredient(s),

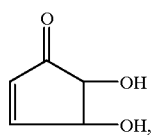

wherein the method uses 4,5-dihydroxy-2-cyclopenten-1-one represented by the formula [1] obtained by the method according to claim 2 as effective ingredient(s).

19. A method for the induction of apoptosis which is characterized in using 4,5-dihydroxy-2-cyclopenten-1-one represented by the formula [1] and/or an optically active compound thereof as effective ingredient(s),

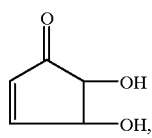

wherein the method uses 4,5-dihydroxy-2-cyclopenten-1-one represented by the formula [1] obtained by the method according to claim 1 as effective ingredient(s).

20. A method for the induction of apoptosis which is characterized in using 4,5-dihydroxy-2-cyclopenten-1-one represented by the formula [1] and/or an optically active compound thereof as effective ingredient(s),

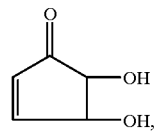

wherein the method uses the heat-treated product according to claim 1 as effective ingredient(s).

21. A method for the induction of apoptosis which is characterized in using 4,5-dihydroxy-2-cyclopenten-1-one represented by the formula [1] and/or an optically active compound thereof as effective ingredient(s),

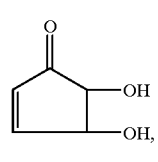

wherein the method uses 4,5-dihydroxy-2-cyclopenten-1-one represented by the formula [1] obtained by the method according to claim 2 as effective ingredient(s).

22. Food or beverage which is characterized in that 4,5-dihydroxy-2-cyclopenten-1-one represented by the formula [1] and/or an optically active compound thereof are/is contained therein, diluted thereby and/or added thereto,

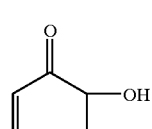

wherein 4,5-dihydroxy-2-cyclopenten-1-one represented by the formula [1] obtained by the method according to claim 1 is contained therein, diluted thereby and/or added thereto.

23. Food or beverage which is characterized in that 4,5-dihydroxy-2-cyclopenten-1-one represented by the formula [1] and/or an optically active compound thereof are/is contained therein, diluted thereby and/or added thereto,

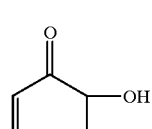

wherein the heat-treated product according to claim 1 is contained therein, diluted thereby and/or added thereto.

24. Food or beverage which is characterized in that 4,5-dihydroxy-2-cyclopenten-1-one represented by the formula [1] and/or an optically active compound thereof are/is contained therein, diluted thereby and/or added thereto,

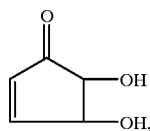

wherein 4,5-dihydroxy-2-cyclopenten-1-one represented by the formula [1] obtained by the method according to claim 2 is contained therein, diluted thereby and/or added thereto.

25. A method of manufacturing 4,5-dihydroxy-2-cyclopenten-1-one according to claim 1 or 2 wherein uronic acid is galacturonic acid, glucuronic acid, guluronic acid, mannuronic acid and/or iduronic acid.

26. A method of manufacturing 4,5-dihydroxy-2-cyclopenten-1-one according to claim 1 or 2 wherein the saccharide compound is a saccharide compound which is selected from pectin, pectic acid, alginic acid, hyaluronic acid, heparin, heparan sulfate, fucoidan, chondroitin sulfate, chondroitin, dermatan sulfate and/or decomposed product thereof.

27. A method of manufacturing 4,5-dihydroxy-2-cyclopenten-1-one according to claim 1 or 2 wherein the heat-treated product is obtained by heating at 60–350° C. for several seconds to several days.

28. A method of manufacturing 4,5-dihydroxy-2-cyclopenten-1-one according to claim 1 or 2 wherein the heat-treated product is obtained by heating under acidic to neutral conditions.

29. A method of manufacturing an optically active compound of 4,5-dihydroxy-2-cyclopenten-1-one according to claim 3 wherein uronic acid is galacturonic acid, glucuronic acid, guluronic acid, mannuronic acid and/or iduronic acid.

30. A method of manufacturing an optically active compound of 4,5-dihydroxy-2-cyclopenten-1-one according to claim 3 wherein the saccharide compound is a saccharide compound which is selected from pectin, pectic acid, alginic acid, hyaluronic acid, heparin, heparan sulfate, fucoidan, chondroitin sulfate, chondroitin, dermatan sulfate and/or decomposed product thereof.

31. A method of manufacturing an optically active compound of 4,5-dihydroxy-2-cyclopenten-1-one according to claim 3 wherein the heat-treated product is obtained by heating at 60–350° C. for several seconds to several days.

32. A method of manufacturing an optically active compound of 4,5-dihydroxy-2-cyclopenten-1-one according to claim 3 wherein the heat-treated product is obtained by heating under acidic to neutral conditions.

33. The (−)-4,5-dihydroxy-2-cyclopenten-1-one having an optical rotation $[\alpha]_D^{20}$ −105° (c=0.30, ethanol).

34. The (+)-4,5-dihydroxy-2-cyclopenten-1-one having an optical rotation $[\alpha]_D^{20}$ of +104° (c=0.53, ethanol).

35. An anticancer agent which is characterized in containing 4,5-dihydroxy-2-cyclopenten-1-one represented by the formula [1] and/or an optically active compound thereof,

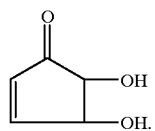

36. A cancer cell differentiation inducer which is characterized in containing 4,5-dihydroxy-2-cyclopenten-1-one represented by the formula [1] and/or an optically active compound thereof,

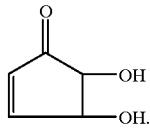

37. An apoptosis inducer which is characterized in containing 4,5-dihydroxy-2-cyclopenten-1-one represented by the formula [1] and/or an optically active compound thereof,

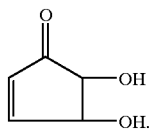

38. An antibacterial agent which is characterized in containing 4,5-dihydroxy-2-cyclopenten-1-one represented by the formula [1] and/or an optically active compound thereof,

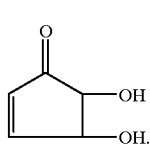

39. An antiseptic which is characterized in containing the antibacterial agent according to claim 38 as effective ingredient(s).

40. A dentifrice which is characterized in containing the antibacterial agent according to claim 38 as effective ingredient(s).

41. A cosmetic which is characterized in containing the antibacterial agent according to claim 38 as effective ingredient(s).

42. A bathing agent which is characterized in containing the antibacterial agent according to claim 38 as effective ingredient(s).

43. A method for the induction of cancer cell differentiation which is characterized in using 4,5-dihydroxy-2-cyclopenten-1-one represented by the formula [1] and/or an optically active compound thereof as effective ingredient(s),

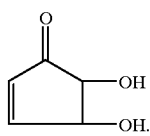

44. A method for the induction of apoptosis which is characterized in using 4,5-dihydroxy-2-cyclopenten-1-one represented by the formula [1] and/or an optically active compound thereof as effective ingredient(s),

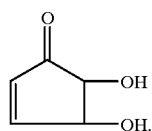

[1]

45. Food or beverage which is characterized in that 4,5-dihydroxy-2-cyclopenten-1-one represented by the formula [1] and/or an optically active compound thereof are/is contained therein, diluted thereby and/or added thereto,

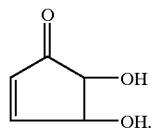

[1]

46. Food or beverage according to claim 45 which is characterized in that 4,5-dihydroxy-2-cyclopenten-1-one represented by the formula [1] and/or an optically active compound thereof is contained in an amount of $5 \times 10^{-6}$ parts or more per 100 parts thereof.

47. Food or beverage according to claim 45 which is an anticancer food and/or an anticancer beverage.

48. Food or beverage according to claim 45 which is antibacterial food and/or antibacterial beverage.

49. A substance which contains a saccharide compound containing uronic acid and/or uronic acid derivative(s) which is characterized in that, in said substance which contains a saccharide compound containing uronic acid and/or uronic acid derivative(s), at least a part of reactivity of amines, amino acids, peptides or protein having a reactivity with uronic acid, uronic acid derivative(s), an intermediate for 4,5 -dihydroxy-2-cyclopenten-1-one represented by the formula [1] or 4,5-dihydroxy-2-cyclopenten-1-one represented by the formula [1] disappears and/or at least a part of said reactive substance(s) is removed,

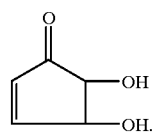

[1]

50. The substance which contains a saccharide compound containing uronic acid and/or uronic acid derivative(s) according to claim 45 which is characterized in that by dry heating treatment, at least a part of reactivity of amines, amino acids, peptides or protein having a reactivity with uronic acid, uronic acid derivative(s), an intermediate for 4,5-dihydroxy-2-cyclopenten-1-one represented by the formula [1] or 4,5-dihydroxy-2-cyclopenten-1-one represented by the formula [1] disappears and/or at least a part of said reactive substance(s) is removed.

51. The substance which contains a saccharide compound containing uronic acid and/or uronic acid derivative(s) according to claim 50 which is characterized in that, the dry heating treatment is conducted by roasting/parching the substance which contains a saccharide compound containing uronic acid and/or uronic acid derivative(s) with hot air of 60–400° C. for several seconds to several days.

52. The substance which contains a saccharide compound containing uronic acid and/or uronic acid derivative(s) according to claim 51 which is characterized in that the substance which contains a saccharide compound containing uronic acid and/or uronic acid derivative(s) is selected from roasted/parched plants, animals or microorganisms.

53. The substance which contains a saccharide compound containing uronic acid and/or uronic acid derivative(s) according to claim 52 which is characterized in that the substance which contains a saccharide compound containing uronic acid and/or uronic acid derivative(s) is selected from roasted/parched vegetables, fruits, cereals, mushrooms, sea algae, cortex or cartilage.

54. The substance which contains a saccharide compound containing uronic acid and/or uronic acid derivative(s) according to claim 49 which is characterized in that by protease treatment, at least a part of reactivity of amines, amino acids, peptides or protein having a reactivity with uronic acid, uronic acid derivative(s), an intermediate for 4,5-dihydroxy-2-cyclopenten-1-one represented by the formula [1] or 4,5-dihydroxy-2-cyclopenten-1-one represented by the formula [1] disappears and/or at least a part of said reactive substance(s) is removed.

* * * * *